United States Patent [19]
Kelln et al.

[11] Patent Number: 5,270,211
[45] Date of Patent: Dec. 14, 1993

[54] SAMPLE TUBE ENTRY PORT FOR A CHEMICAL ANALYZER

[75] Inventors: Norman Kelln; Kelsey Loughlin, both of Spokane; Bruce Weyrauch, Newman Lake, all of Wash.

[73] Assignee: Schiapparelli Biosystems, Inc., Fairfield, N.J.

[21] Appl. No.: 916,222

[22] Filed: Jul. 16, 1992

[51] Int. Cl.$^5$ .................. G01N 35/00; G01N 21/00; G01N 1/00
[52] U.S. Cl. .................. 436/43; 436/49; 436/54; 436/180; 422/63; 422/64; 422/100; 73/863.23; 73/863.24; 73/864.83; 73/864.85; 73/864.86; 73/864.87
[58] Field of Search .................. 422/63, 64, 100; 436/43, 49, 54, 180; 356/246; 73/863.23, 863.24, 864.85, 864.86, 864.87, 863.83

[56] References Cited

U.S. PATENT DOCUMENTS

| | | | |
|---|---|---|---|
| 2,503,147 | 4/1950 | Applezweig | 226/116 |
| 3,641,823 | 2/1972 | Harris, Sr. et al. | 73/425.4 |
| 4,274,453 | 6/1981 | Lee | 141/1 |
| 4,475,411 | 10/1984 | Wellerfors | 73/864.24 |
| 4,478,095 | 10/1984 | Bradley et al. | 73/864.21 |
| 4,539,855 | 9/1985 | Jacobs | 73/864.25 |
| 4,577,514 | 3/1986 | Bradley et al. | 73/863.01 |
| 4,624,148 | 11/1986 | Averette | 73/864.23 |
| 4,691,580 | 9/1987 | Fosslien | 73/864.84 |
| 4,713,974 | 12/1987 | Stone | 73/864.23 |
| 4,721,137 | 1/1988 | Muller | 141/65 |
| 4,737,150 | 4/1988 | Baeumle et al. | 604/198 |
| 4,834,944 | 5/1989 | Wakatake | 422/64 |
| 4,927,545 | 5/1990 | Roginski | 210/745 |
| 4,951,512 | 8/1990 | Mazza et al. | 73/861.23 |
| 4,961,906 | 10/1990 | Andersen et al. | 422/102 |
| 5,130,254 | 7/1992 | Collier et al. | 436/54 |
| 5,163,582 | 11/1992 | Godoephin et al. | 222/1 |
| 5,169,602 | 12/1992 | Pang et al. | 422/103 |

OTHER PUBLICATIONS

CAMAG Brochure "Automatic TLC Sampler III".
CleanTech Brochure "How to use the CleanTech System".
Supplemental Information Disclosure Statement from the file of U.S. patent appl. Ser. No. 210,695 (now U.S. Pat. No. 4,951,512).

*Primary Examiner*—James C. Housel
*Assistant Examiner*—N. Bhat
*Attorney, Agent, or Firm*—Wells, St. John, Roberts, Gregory & Matkin

[57] ABSTRACT

A sample tube entry port for an automatic chemical analyzer supports individual draw tubes that are manually delivered to the analyzer at a sample access station. The entry port facilitates removal of samples by the pipette without exposing operating personnel to accidental contact with liquid materials in the draw tube. To accommodate draw tubes of differing heights, the apparatus includes a stripper that is selectively locked onto an elevationally movable ram carrying a receptacle for receiving a draw tube. A spring-biased tube clamp urges each draw tube against guides within the receptacle to center draw tubes of differing diameters. During operation of the apparatus, the receptacle is first lowered to a predetermined elevation, then raised to an intermediate elevation at which a draw tube closure is properly positioned for placement of the stripper immediately adjacent to its upper surface. The stripper is locked relative to the ram in this elevational relationship, which is maintained as the closure is impaled on the puncture tube and/or the pipette that accesses the contents of the draw tube.

12 Claims, 21 Drawing Sheets

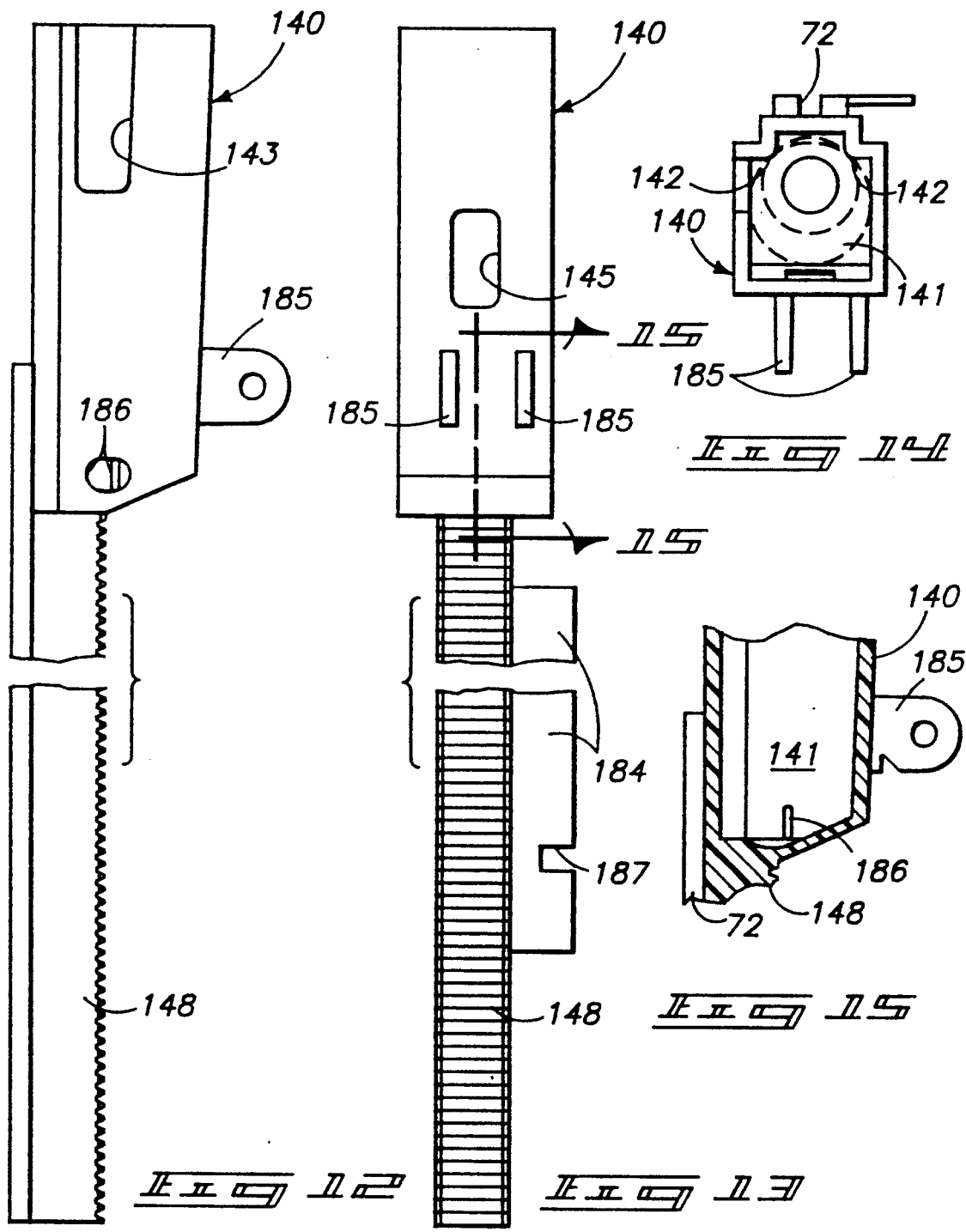

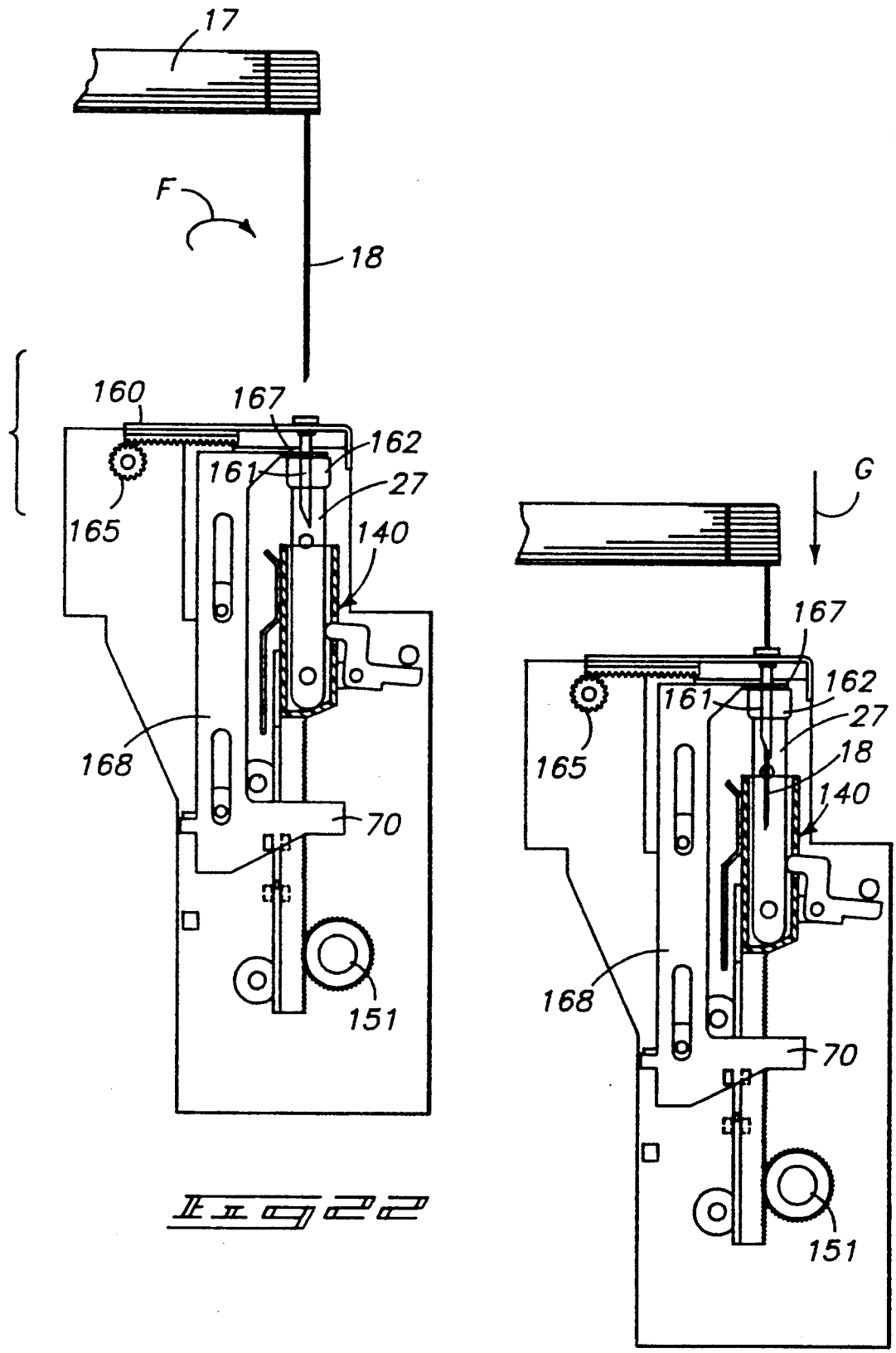

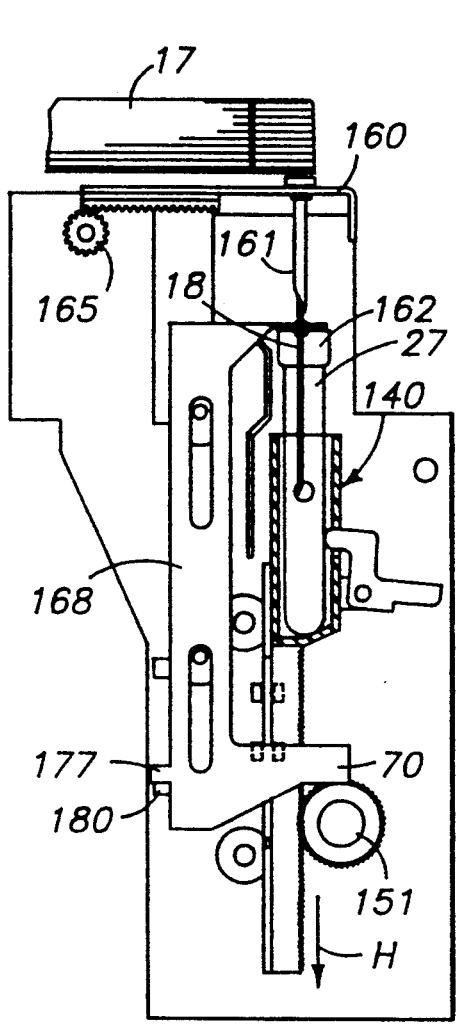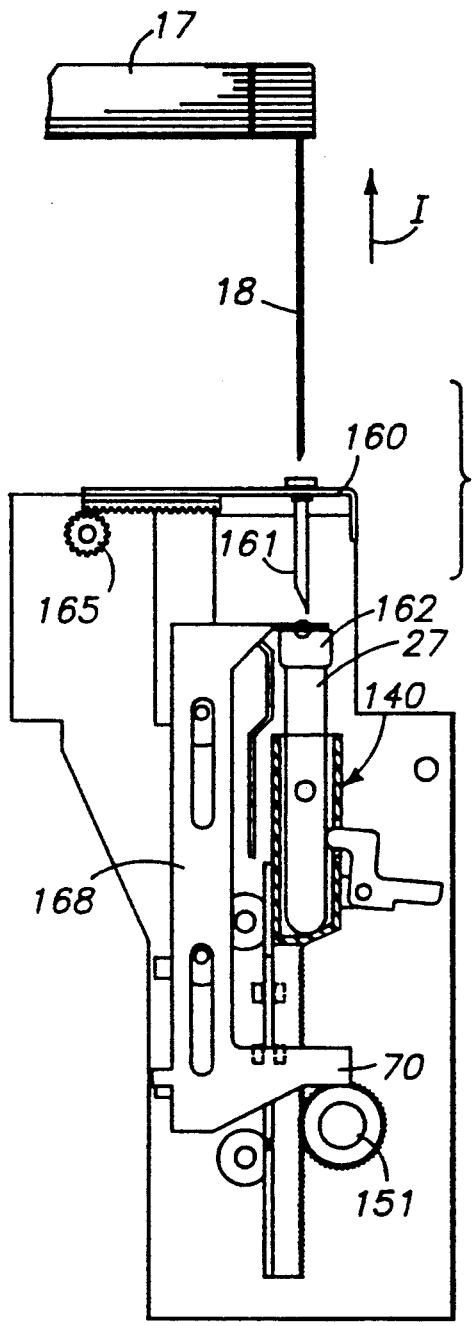

| TURNTABLE 11 | STATIONARY | MIX | ACCEL-ERATE | SPIN | | DECEL-ERATE |
|---|---|---|---|---|---|---|
| PROBE ARM 17 | DISPENSE FLUID | WASH (SHORT) | | | | |
| MAGAZINE 75 | INSERT CUVETTE | | | | | |
| OPTICAL SYSTEM 14 | MOVE FILTER OUT / TRANSMIT DATA | | | ABSORBANCE READINGS | MOVE FILTER IN | FLOUR-ESCENCE READINGS |

FIG. 30

SAMPLE TUBE ENTRY PORT FOR A CHEMICAL ANALYZER

TECHNICAL FIELD

This disclosure relates to automatic chemical analyzers for directly measuring properties of reacted liquids to produce qualitative and quantitative analyses of tested samples. A sample tube entry port is disclosed that delivers liquid from a draw tube to a clinical chemistry analyzer. A typical use of such an analyzer might be testing of patient blood or urine samples.

BACKGROUND OF THE INVENTION

Automated analyzers have been developed for biochemical analysis of patient samples, such as whole blood, serum, urine, plasma and cerebral spinal fluid. Most such equipment available today is large, complicated to operate, and high in cost.

Operating such equipment is technically complicated. It typically requires specialized operators to be always available. It is usually designed for use by large laboratories serving a wide geographic area or by a large medical facility. Existing analyzers normally carry out tests in a defined sequence designed for efficient, high volume usage.

Such large scale capacity is not always required. This is particularly true in smaller medical clinic settings where large volumes of blood sample tests are not required on a daily basis.

The present chemical analyzer was developed to meet the practical needs of smaller medical settings. It is designed as a desk-top unit that can be operated without specialized laboratory training. Its capacity is adequate for meeting typical clinical applications. As an example, it can be designed to produce a maximum of 164 test results per hour for routine, single reagent chemistries. To provide a representative wide number of reagents, the analyzer has been designed to have a capacity of 40 reagent containers of two different sizes. Its capacity can be effectively doubled by using two chemistry instruments in tandem, both being controlled by a common workstation.

The compact nature of the analyzer can be partially attributed a single probe arm and pipette servicing all of the functional liquid-handling components included within it. The pipette is used for transferring both samples and reagents, as well as for diluting liquids as needed by particular test requirements.

To obtain large volumes of tests, conventional laboratory analyzers are programmed to conduct test procedures in a fixed sequence of events. While predetermined test sequences are practical in high volume chemical analyzer applications, there is a need for more flexible operation when scaling such test procedures to meet the needs of smaller medical facilities.

Most automated analyzers that accommodate samples provided in conventional draw tubes require that such tubes be delivered into the machine in carrousels or on a dedicated conveyor. The draw tubes are then processed as a group over a significant dwell time within the equipment. One feature desirable in many clinical settings is the ability to aliquot samples from a conventional draw tube without requiring the continued presence of the draw tube during the subsequent test sequences. This permits the sample material in the tube to be used simultaneously in other test procedures. For this reason, the present sample tube entry port has been designed to remove a sample promptly upon receipt of a draw tube. It then immediately releases the draw tube for any other current purposes required in the setting in which the chemical analyzer is used.

The sample tube entry port has been designed to facilitate automatic aliquoting of samples from conventional sealed draw tubes without destroying the seals closing the draw tubes. It also protects personnel from accidental contact with the sampled materials. The entry port automatically accommodates draw tubes differing from one another in both tube diameter and length.

Further details will be clear from the following description.

BRIEF DESCRIPTION OF THE DRAWINGS

Preferred embodiments of the invention are described below with reference to the accompanying drawings, which are briefly described below.

FIG. 12 is a fragmentary side elevation of the ram;

FIG. 13 is a front view;

FIG. 14 is a top view;

FIG. 15 is a sectional view taken along line 15—15 in FIG. 13;

FIGS. 16–28 are a series of diagrammatic views illustrating operation of the sample tube entry port;

FIG. 16 illustrates the initial "home" position;

FIG. 17 illustrates reception of a draw tube;

FIG. 18 illustrates the extreme lowered position of the ram;

FIG. 19 illustrates initial elevation of the draw tube;

FIG. 20 illustrates closing of the cover;

FIG. 21 illustrates puncturing of the tube stopper;

FIG. 22 illustrates initial placement of the probe arm;

FIG. 23 illustrates insertion of the pipette;

FIG. 24 illustrates initial lowering of the draw tube;

FIG. 25 illustrates removal of the pipette;

FIG. 26 illustrates opening of the cover;

FIG. 27 illustrates removal of the draw tube;

FIG. 28 illustrates the final "home" position of the ram;

FIG. 30 is a timing diagram for the instrument components.

DETAILED DESCRIPTION OF THE PREFERRED EMBODIMENT

Figure 1:
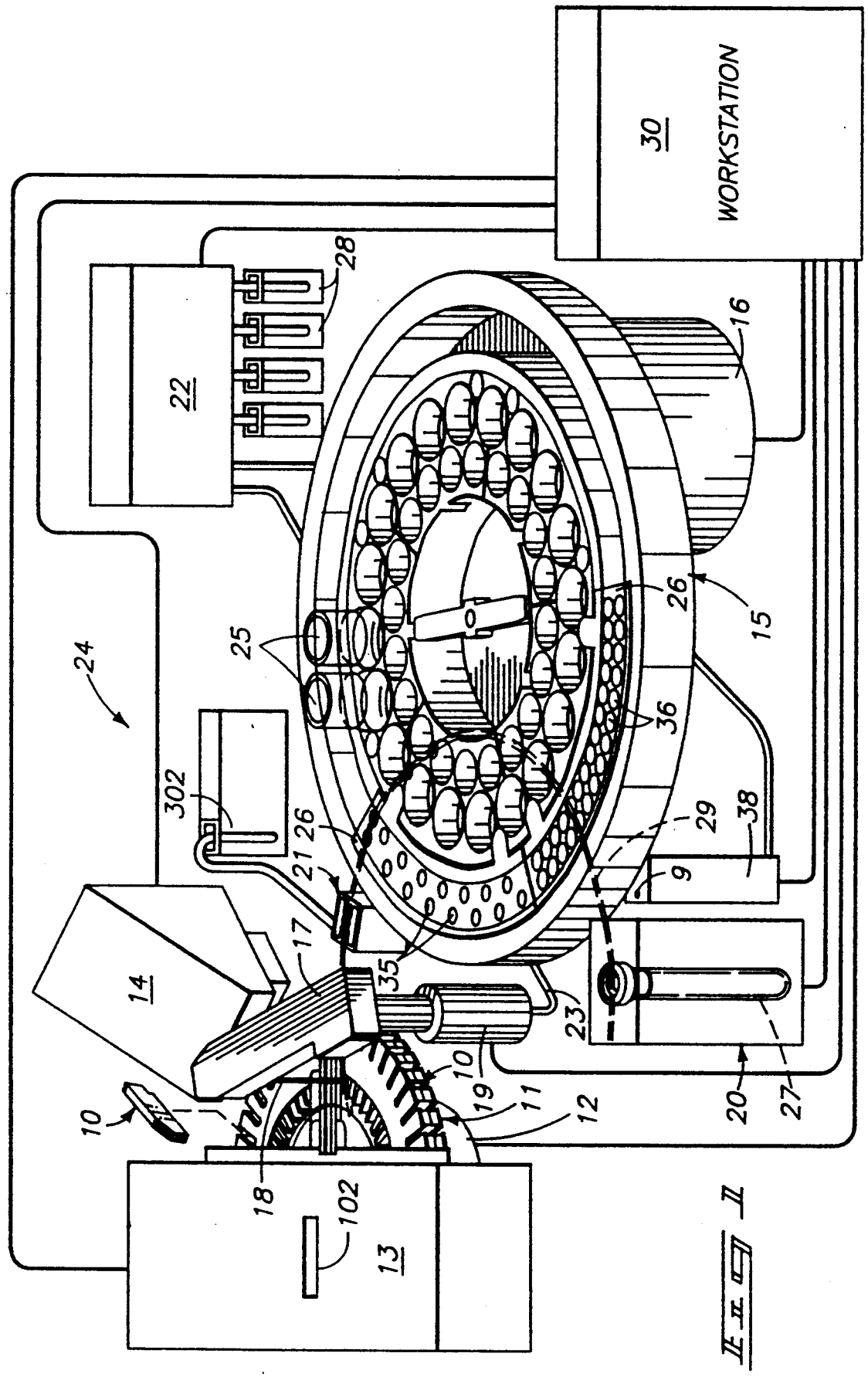
FIG. 1 is a diagrammatic perspective view of the principal components in the analyzer.

This disclosure of the invention is submitted in furtherance of the constitutional purposes of the U.S. Patent Laws "to promote the progress of science and useful arts" (Article 1, Section 8).

System Overview

The automatic chemical analyzer (generally illustrated in FIGS. 1-3) includes a turntable 11 rotatably mounted about a first vertical axis. A plurality of disposable cuvettes 10 are releasably mounted to the turntable 11. A first power means, shown as motor 12, is operably connected to turntable 11 for alternately (1) indexing it at a stationary angular position about the first axis with a selected cuvette 10 positioned at a cuvette access station A or (2) turning it about the first axis while mixing or centrifuging contents of cuvettes mounted to it.

First analytical means, illustrated as an optical system 14, is provided adjacent to the turntable 11 for performing tests on the contents of the cuvettes 10 as they rotate about the turntable axis.

A tray 15 is rotatably mounted about a second vertical axis parallel to and spaced from the axis. A plurality of containers 25, 35, and 36 are positioned about tray 15 for reception of samples and reagent liquids. Second power means, illustrated as motor 16, is operably connected to the tray 15. The motor 16 indexes tray 15 to a stationary angular position about the second axis with a selected container positioned at a container access station C.

The analyzer also includes a probe arm 17 movable about a third vertical axis parallel to the first axis. Probe arm 17 supports a downwardly-extending open pipette 18. The vertical pipette 18 is movable along an arcuate path centered about the third axis and intersecting both the cuvette access station A and container access station C. It can move along the arcuate path in a random fashion to transfer liquid from a container positioned on the tray at the container access station C to a cuvette 10 positioned on the turntable 11 at the cuvette access station A. The arcuate path of the pipette 18 can be visualized along a protective groove 29 formed at the exterior of the enclosure 39 housing the chemistry instrument 24.

The illustrated embodiment of the clinical chemistry analyzer consists of two major components: a chemistry instrument 24 and a workstation 30. The chemical instrument accepts liquid patient samples for testing purposes, performs appropriate optical and/or potentiometric measurements on the samples, and communicates the resulting test data to workstation 30. Workstation 30 is used by the operator to enter data, control operation of instrument components, accept data generated by the instrument, manage and maintain system information, and generate visual and printed reports about assays and instrument performance.

The chemistry instrument 24 is a separate unit with minimal operator controls. Either one or two identical chemistry instruments 24 can be linked to a single workstation 30, as required in a particular setting. The chemistry instrument 24 can perform several types of analysis. These include routine chemistries, electrolytes, therapeutic drug monitoring, drugs of abuse in urine, and other specialized tests.

The liquid-handling components that make up the chemistry instrument 24 are housed within enclosure 39 (FIGS. 2-5). It separates along a peripheral parting line 37 defining a lower supporting base 33 and an upper hinged cover 34.

Figure 2:
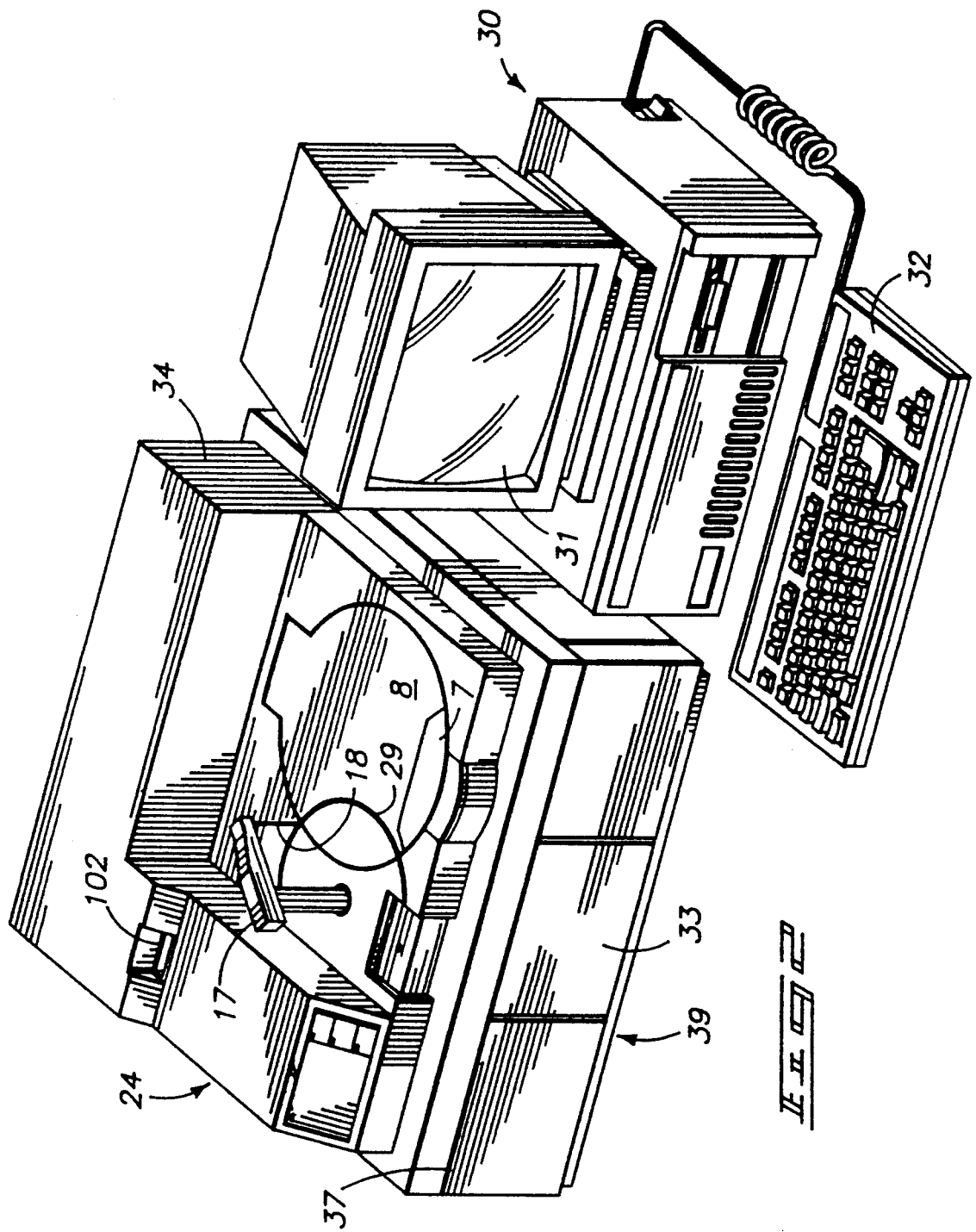
FIG. 2 is a perspective view of the analyzer.

The principal modular components of the chemistry instrument 24 are diagrammatically illustrated in FIG. 1. The illustrated components are specifically designed for use in association with a specially designed liquid cuvette 10.

A computerized operator interface to the chemistry instrument 24 is provided through connections to the programmable workstation 30. Most of the operator interactions with the analyzer take place at workstation 30. It is an external desktop computer located near the chemistry instrument(s) 24. It uses an industry standard operating system and bus structure, plus a hard disk. It is also provided with a custom instrument interface board for each associated chemistry instrument.

Operations required for sample testing of cuvette contents are not carried out in any predetermined sequence dictated by insertion of a sample into the chemistry instrument 24. Instead, workstation 30 serves as random access control means operably connected to the turntable 11, tray 15 and probe arm 17 for selectively transferring liquid from any container on the tray 15 to any cuvette 10 on the turntable 11 according to defined logical priority rules programmed into the workstation.

Operations carried out within the chemistry instrument 24 are timed about a repetitious cycle of operations. Each cycle involves sequentially transferring liquids to an awaiting cuvette 10 on the turntable 11, mixing the liquids, and centrifuging them for test purposes.

A monitor 31 is included within workstation 30 to display data, messages and optional menus for the operator. A keyboard 32 is included for operator input of data and instructions. A printer (not shown) of conventional design can also be provided in the system to record tests results and reports as required.

A plurality of test cuvettes 10 are releasably located within a motor-controlled turntable 11. It is powered by a DC motor 12. Motor 12 can be accurately controlled to (1) selectively index turntable 11 at a chosen angular position about its vertical axis for access to a particular cuvette and/or insertion of new cuvettes or (2) intermittently or reversibly rotate turntable 11 about its axis for mixing the contents of the cuvettes or (3) spin turntable 11 for centrifuging the contents of the cuvettes during photometric analysis.

A liquid transfer module includes a single probe arm 17 movably supported on the instrument 24 about a vertical axis. The outer end of probe arm 17 carries a downwardly extending pipette 18. Pipette 18 is used for transferring liquids between various locations about the chemistry instrument. Its lower or outer end is open for receiving or discharging liquids.

Probe arm 17 is supported and powered by a positioning assembly 19. The positioning assembly 19 has two stepper motors—one for imparting rotational motion to probe arm 17 and one for imparting vertical motion to it. Positioning assembly 19 can selectively move probe arm 17 and pipette 18 both angularly and axially relative to the vertical axis of probe arm 17.

The tip or lower end of pipette 18, while in an elevated condition permitting angular movement about the chemistry instrument 24, projects slightly into an open arcuate groove 29 (FIGS. 2, 3) formed about the cover 34 of the instrument enclosure. Groove 29 is centered about the axis of probe arm 17 and is recessed within cover 34. It overlaps the bottom of pipette 18 to prevent its accidental engagement with the hands of an operator as the pipette travels from one station to the next. The protective overlap of the pipette tip eliminates the danger of accidentally impaling adjacent personnel when pipette 18 is subsequently lowered.

A cuvette dispenser module 13 is arranged on the framework of the equipment in a position immediately above the turntable 11. It includes a storage magazine for a plurality of stacks of cuvettes 10. It also includes an apparatus for transferring individual cuvettes 10 from a randomly selectable stack within the magazine 75 to a receiving compartment on turntable 11. Used cuvettes 10 are discarded into a removable cuvette disposal container (not shown) as new cuvettes are delivered to the turntable 11 by operation of a reciprocating ram. The cuvette disposal container can be a bag or bin into which used cuvettes drop when ejected from turntable 11.

The optical system 14 is contained within a housing positioned next to turntable 11. Optical system 14 performs photometric tests on the contents of cuvettes 10 while they are being spun about the turntable axis. The optical system 14 measures both fluorescent emissions and light absorbance by cuvette contents within the turntable 11. Photometric test groups typically supported include routine chemistries, special proteins, therapeutic drugs, and drugs of abuse.

For absorbency tests, the optical system 14 measures radiation at 180 degrees to the incident light. Readings are made at several wavelengths on a diode array, but only those points requested in specified test parameters are processed by the instrument 24. System offsets are subtracted from the results and the sample signal is divided by a reference signal. The negative logarithm of this ratio is the absorbance.

When conducting fluorescent tests, emitted radiation at a wavelength longer than that of the source is measured at 90 degrees to the incident beam. System offsets are subtracted and the intensity is then normalized using a reference signal.

A sample/reagent tray 15 is rotatably mounted about a vertical axis parallel to and spaced from the axis of turntable 11. It is rotatably powered by a stepper motor 16. Tray 15 consists of a circular reagent bottle support surrounded by separate interlocking ring segments 26. The removable ring segments 26 are used to hold reagents and samples required for assay procedures during operation of chemistry instrument 24.

Tray 15 supports a plurality of liquid containers, namely the reagent bottles 25, open cups 35 and open wells 36. The interchangeable ring segments 26 have two alternate configurations. One includes apertures for removably supporting individual sample cups 35. The other includes a plurality of integrally molded sample wells 36.

The individually removable cups 35 serve as containers for test samples supplied to the instrument 24 by the operator within one or more cups within a ring segment 26. Wells 36 are used by the instrument components in conjunction with operation of probe arm 17 for aliquoting of samples from a draw tube and for sample dilution purposes. The probe arm 17 can selectively transfer liquids from one well 36 to a second well 36, from a cup 35 to a well 36, or from a reagent bottle 25 to a well 36.

Access to the sample/reagent tray 15 is provided by a hinged tray access cover 8 formed in the enclosure cover 34. More limited manual access to a single ring segment 26 located at the front of the chemistry instrument 24 is provided by a hinged segment access port 7, which is a sub-assembly of cover 8.

Figure 3:
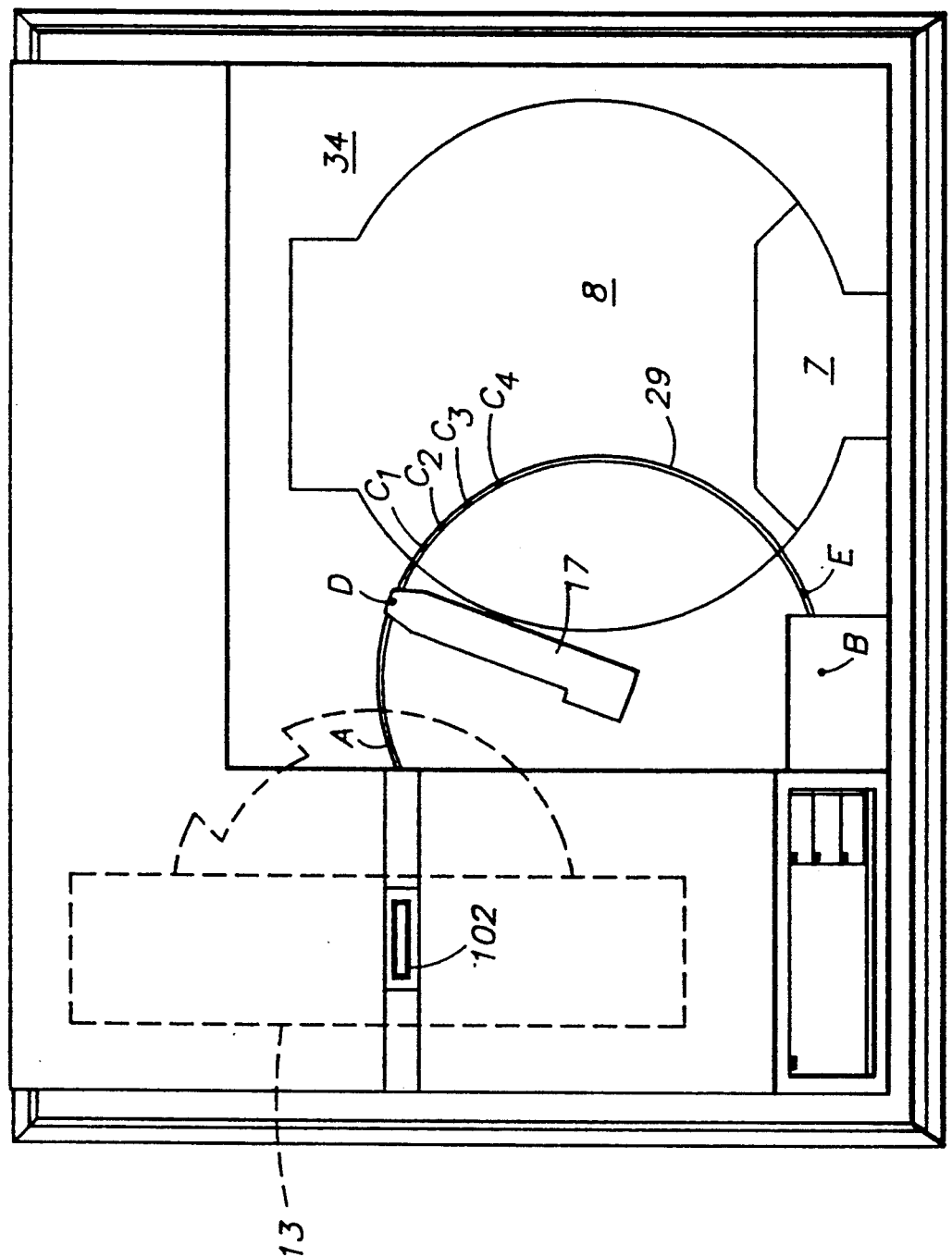
FIG. 3 is a plan view of the chemical instrument enclosure.
Figure 4:
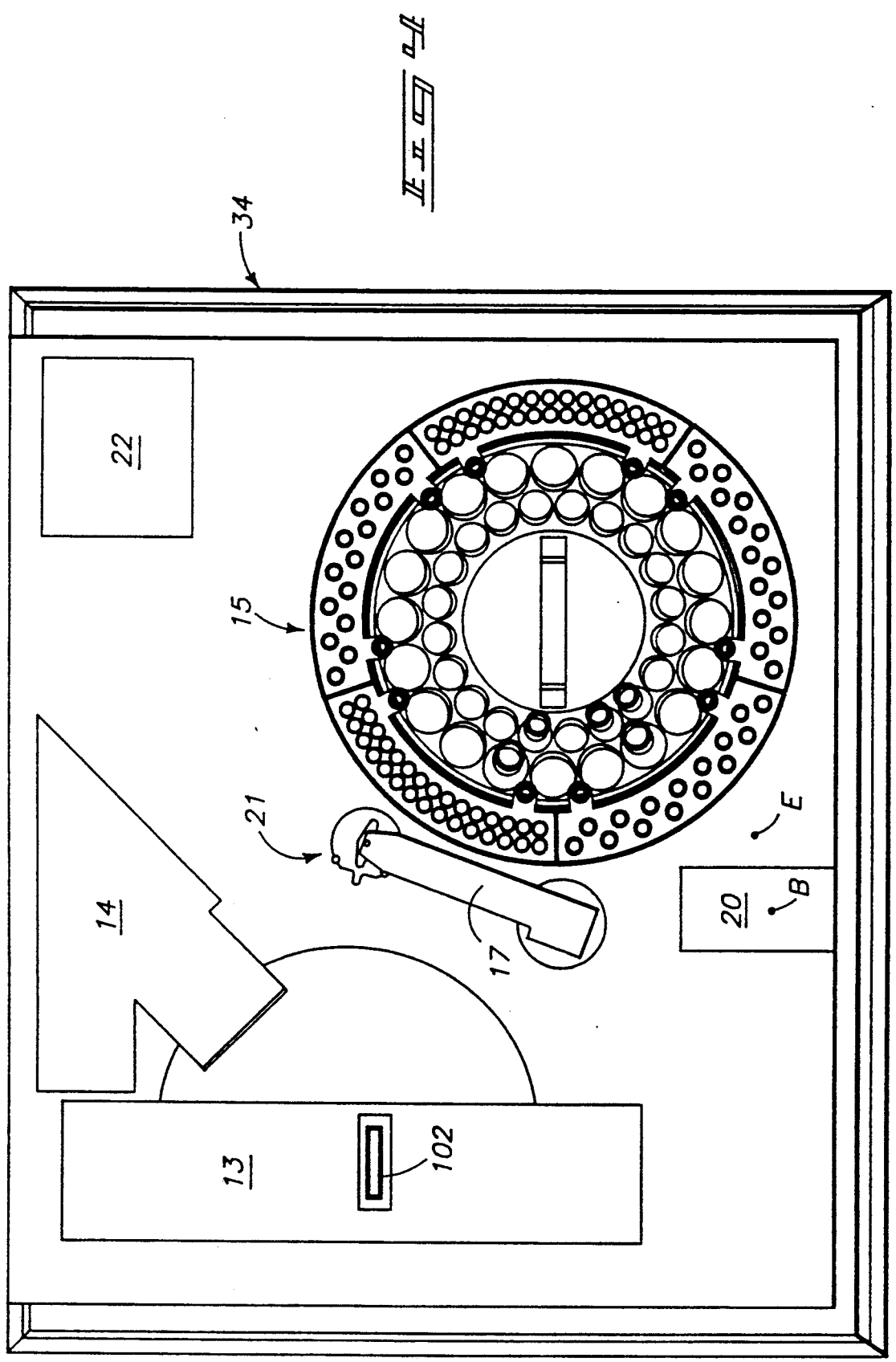
FIG. 4 is a plan view of the chemical instrument enclosure with the cover removed.
Figure 5:
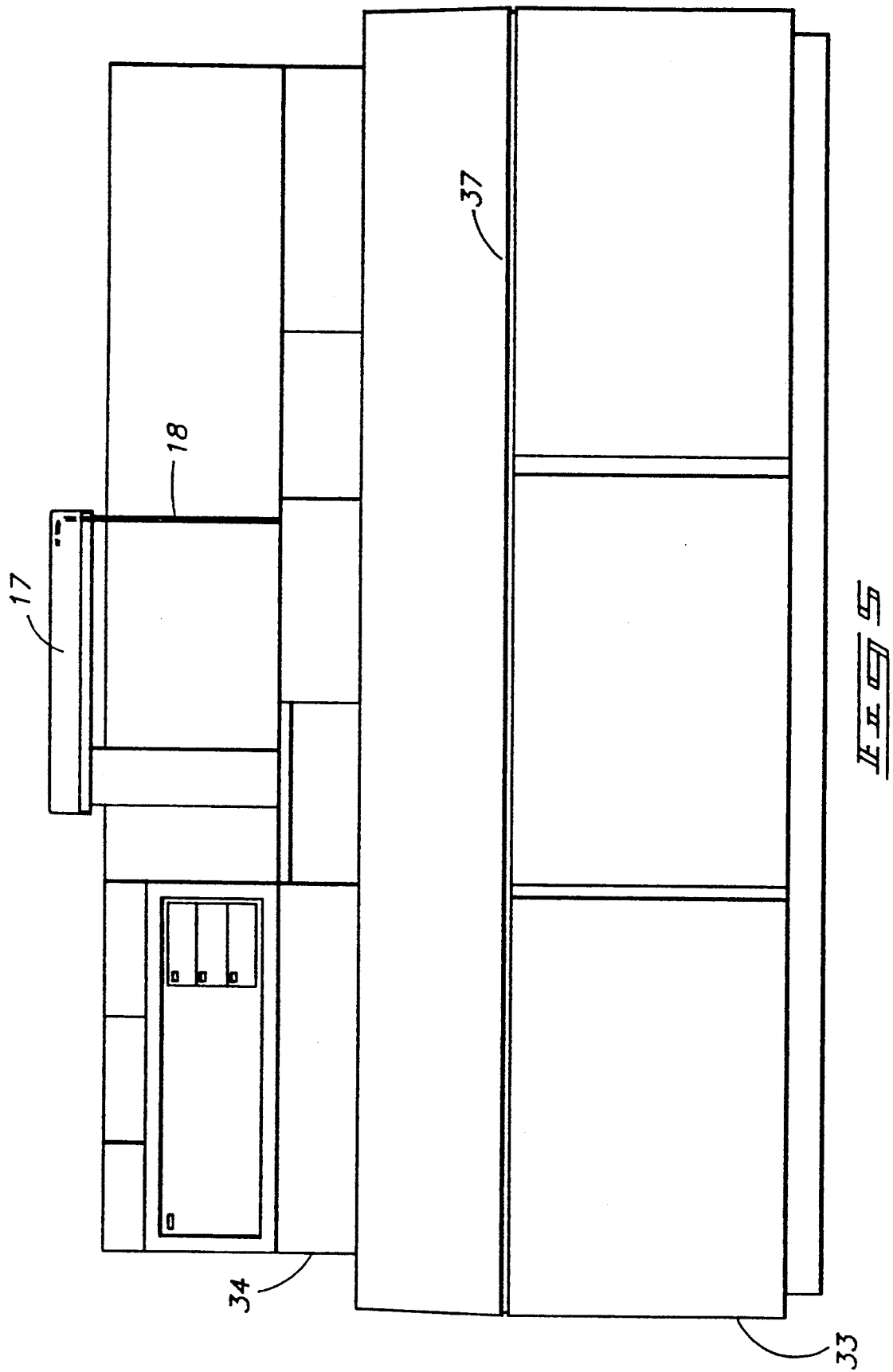
FIG. 5 is a front elevation view of the enclosure.

A stepper motor 16 can be operated to index sample/reagent tray 15 to a selected position about its axis with one or more selected containers at one of four container access stations shown in FIG. 3 at locations $C_1$, $C_2$, $C_3$, $C_4$ on the equipment framework. Each container access station intersects the path of pipette 18, which is coincident with groove 29.

Scanning means is provided next to the tray 15 for capturing identifying information from encoded indicia on a container positioned on it.

A cooling system (not shown) for the chemistry instrument 24 incorporates multiple thermoelectric cooling units. These are needed in the areas of the sample/reagent tray 15 and the turntable 11. Heat can be removed from the system by air exchange through a plurality of heat sinks.

A sample tube entry port 20 is provided on the framework for receiving and supporting successive individual draw tubes 27 as they are introduced into the instrument by the operator. Its primary use is to permit the taking of aliquots from positively identified, sealed patient draw tubes. It can also be used for delivery of control liquids from tubes of a similar exterior configuration, whether covered or open. Positive identification can be provided by an encoded label on each draw tube 27. The label is scanned by a bar code reader included within the sample tube entry port 20.

Each draw tube 27, of conventional design, is sealed by a closure at its upper end. Sample tube entry port 20 supports each manually inserted draw tube 27 while pipette 18 pierces the closure 162 to access liquid sample material from the tube interior. Liquid removal from successive tubes 27 occurs at a sample access station B along the arcuate path 29.

Puncturing means are provided within the sample tube entry port 20 for temporarily forming an opening through a closure on a manually-delivered draw tube 27 placed within it. A ram positioned below the puncturing means receives and coaxially orients a manually placed draw tube 27 relative to the puncturing means. It moves the draw tube parallel to a fourth vertical axis (centered along the puncturing means) between a lowered position wherein the draw tube 27 is clear of the puncturing means and a raised position wherein the puncturing means forms a temporary opening through the draw tube closure for subsequent coaxial insertion of the pipette 18. The interior of the draw tube 27 is then accessible by subsequently inserting pipette 18 coaxially through the puncturing means.

A wash/alignment module 21 is located at a fixed position on the framework. Its first purpose is to provide vertical basins within which the lower end surfaces of pipette 18 can be flushed clean during or after liquid transfer cycles. It also supports a conductive sensing plate that verifies both the radial alignment and elevational position of pipette 18 about the pipette axis on the probe arm 17 for monitoring alignment of the pipette. These operations occur at a wash/alignment station D along the arcuate path 29 of pipette 18.

A capacitive sensing circuit is operably connected to the pipette 18 and to conductive members located next to the tray 15 and within the sample tube entry port 20.

The sensing circuit detects the level of liquid in a container on the tray or a draw tube 27 as it is approached by the pipette.

A second analytical means, shown as an Ion Specific Electrode (ISE) module 38 of conventional design and operation, is included within the chemistry instrument 24. It is illustrated generally in FIG. 1. Potentiometric tests may be requested and run by the ISE module 38 simultaneously with photometric tests being conducted by the optical system 14.

Samples are delivered to the ISE module 38 by pipette 18 at a sample delivery station E along the arcuate path 29 (FIG. 3). Module 38 can include tests for the presence of a variety of analytes, such as sodium, potassium, chloride, lithium or calcium. For each analyte, all sample types are analyzed in the same manner. The different sample types can be loaded using different dilution factors.

The ISE module 38 consists of electrodes specific to the chosen analyte, a reference electrode and the associated fluid system required to process tested samples. The potentiometric measurement consists of a voltage difference between the analyte's electrode and the reference electrode.

Water is supplied to pipette 18 from a syringe module 22 connected to a water supply container in a container rack 28. The syringe module 22 consists of a volume displacement syringe and associated valves leading to a source of water and a waste water container (not shown). It is used for all aspirations of samples, reagents and diluents in the chemistry instrument 24. The syringe module is of conventional design.

Tubing 23 (FIG. 1) connects syringe module 22 to pipette 18. Tubing 23 contains water that can be moved in opposite directions to receive or discharge liquids at the lower end of pipette 18.

The above components are individually operable under control of a distributed computerized controller system governed by the programmable workstation 30. Workstation 30 is electronically linked to the instrument via a bi-directional communications interface. This interface is used to communicate patient requisitions to the chemistry instrument 24 and to receive the associated test results from the instrument 24. All control functions can be randomly initiated under control of scheduling software and logic to match pending requisition requirements and current instrument status conditions.

The external computer can send patient requisitions to the workstation either individually or in ring segment groups. The workstation can send test results to the external computer.

The control system associated with chemistry instrument 24 includes several dedicated microprocessors and programmable memory devices. They individually operate the system components as prioritized by scheduling software residing in the instrument CPU board. The workstation 30 includes monitoring means for maintaining a current record of the amount of liquid in containers on the sample/reagent tray 15. Controlling software associated with the microprocessors causes the mechanical components of the chemistry instrument 24 to carry out all operations efficiently and effectively without operator intervention, using a random sequence of movements dictated by outstanding test requirements.

The arrangement of operational stations along the arcuate path of pipette 18 permits transfer of liquids from a draw tube 27 at the sample access station B to a well 36 at a container access station $C_1$ or $C_2$ on the sample/reagent tray or from a well 36 to a cuvette 10 at the cuvette access station A on turntable 11. Alternately, pipette 18 can transfer sample diluents (buffers) from the reagent bottles 25 at container access stations $C_3$ or $C_4$ on the sample/reagent tray 15 to a well 36 at a container access station $C_1$ or $C_2$. In addition, it can transfer liquids from one well 36 to another, or from a cup 35 to a well 36 for dilution purposes at container access stations $C_1$ or $C_2$. Direct transfer of reagents from bottles 25 to cuvettes 10 can also take place at cuvette access station A. A wash or pipette alignment procedure can also be periodically accomplished at wash/alignment station D as required. ISE tests are initiated by optional delivery of sample liquids to the ISE station E.

Sample Tube Entry Port

Test samples can be individually delivered by the operator to a chemistry instrument 24 within a conventional draw tube 27 having a resealable stopper or closure 162. Manual delivery of a draw tube 27 to the sample tube entry port 20 initiates requisitioned tests relating to the liquid sample (blood, urine) contained within it. Removal of sample liquid from tube 27 is accomplished without destroying the seal provided by closure 162, which is of a type normally provided on draw tubes used for blood sampling purposes.

Sample tube entry port 20 is constructed as an operational module detailed in FIGS. 6–15. It is designed to receive and handle draw tubes 27 of differing lengths and diameters. It temporarily punctures the stopper of each draw tube 27, providing an opening through a puncture tube 161 for entry of pipette 18. The closure 162 on the draw tube 27 later reseals itself and wipes the exterior surfaces of both the puncture tube 161 and the pipette 18 as they are retracted outwardly from it.

The sample tube entry port 20 is designed about an elevationally movable ram 140 having an upwardly open receptacle 141 for holding a single draw tube 27. The ram 140 is detailed in FIGS. 12–15.

Sample tube entry port 20 is shown in FIGS. 6–10 with a receiving draw tube ram 140 at its "home" position. This is the position in which draw tubes are manually inserted into or removed from chemistry instrument 24. Operation of the sample tube entry port 20 is diagrammatically illustrated in FIGS. 16–28.

The module enclosure includes two spaced vertical side walls 152 and 153. These walls are transversely spanned by a front wall 154 and a rear wall 155. A forward horizontal flange 156 serves as a partial cover for the mechanism within the enclosure. A horizontally movable access cover 160 is slidably guided by rods 157 at each side of the enclosure.

One side of ram 140 has an open slot 143 leading to receptacle 141. Encoded information on labels applied to a draw tube 27 can be accessed through the slot 143 and read by a scanner 144. Transversely open apertures 186 also extend though the ram 140 next to the bottom end of receptacle 141. The presence of a draw tube 27 within ram 140 is detected by line of sight sensors 189 aligned with the apertures 186 and mounted on the opposed side walls 152, 153 of this module.

The bottom end of receptacle 141 is concavely dished to help in supporting draw tubes 27 of differing diameters. Receptacle 141 is also provided with two vertical ribs 142 along its back. They engage and transversely center draw tubes 27 of differing diameters, as shown by the circles drawn in dashed lines in FIG. 14.

The front of ram 140 is apertured at 145 to access the interior of receptacle 141. Two protruding brackets 185 are located below the aperture 184. A spring-biased tube clamp 146 is pivoted between brackets 185 about a transverse pivot shaft 147 extending between the side walls 152 and 153. The tube clamp 146 is spring-biased to an inner position projecting inwardly through recess 145, at which it engages the centerline of a draw tube 27 located within receptacle 141.

The inward pressure exerted on a draw tube 27 by the spring-biased tube clamp 146 urges it rearwardly toward the two spaced centering ribs 142. This action transversely centers each draw tube 27 within ram 140 regardless of its diameter. Tube clamp 146 then yieldably holds tube 27 in a fixed position within ram 140 during later sampling procedures.

Tube clamp 146 includes an integral forwardly-projecting tab 149. A transverse rod 159 extends from side wall 152 of the module enclosure across the vertical path of movement of the tab 149. Engagement of tab 149 by the stationary rod 159 will result in outward movement of finger 147 from within receptacle 141 of ram 140 at the upper limit of movement of ram 140.

A rigid vertical rack 148 extends downwardly from ram 140. The rear surface of rack 148 has a vertical groove 72 formed along it. Groove 72 receives two guide rollers 150, which act in opposition to a driving gear 151 that meshes with the teeth formed across the front of rack 148 to support the rack 148 and ram 140. Gear 151 is powered by a DC motor 163 located on the outer surface of side wall 152. The combination of gear 151 and rollers 150 maintains ram 140 in a constant vertical orientation throughout the limits of its vertical movement relative to the supporting module enclosure.

Figure 6:
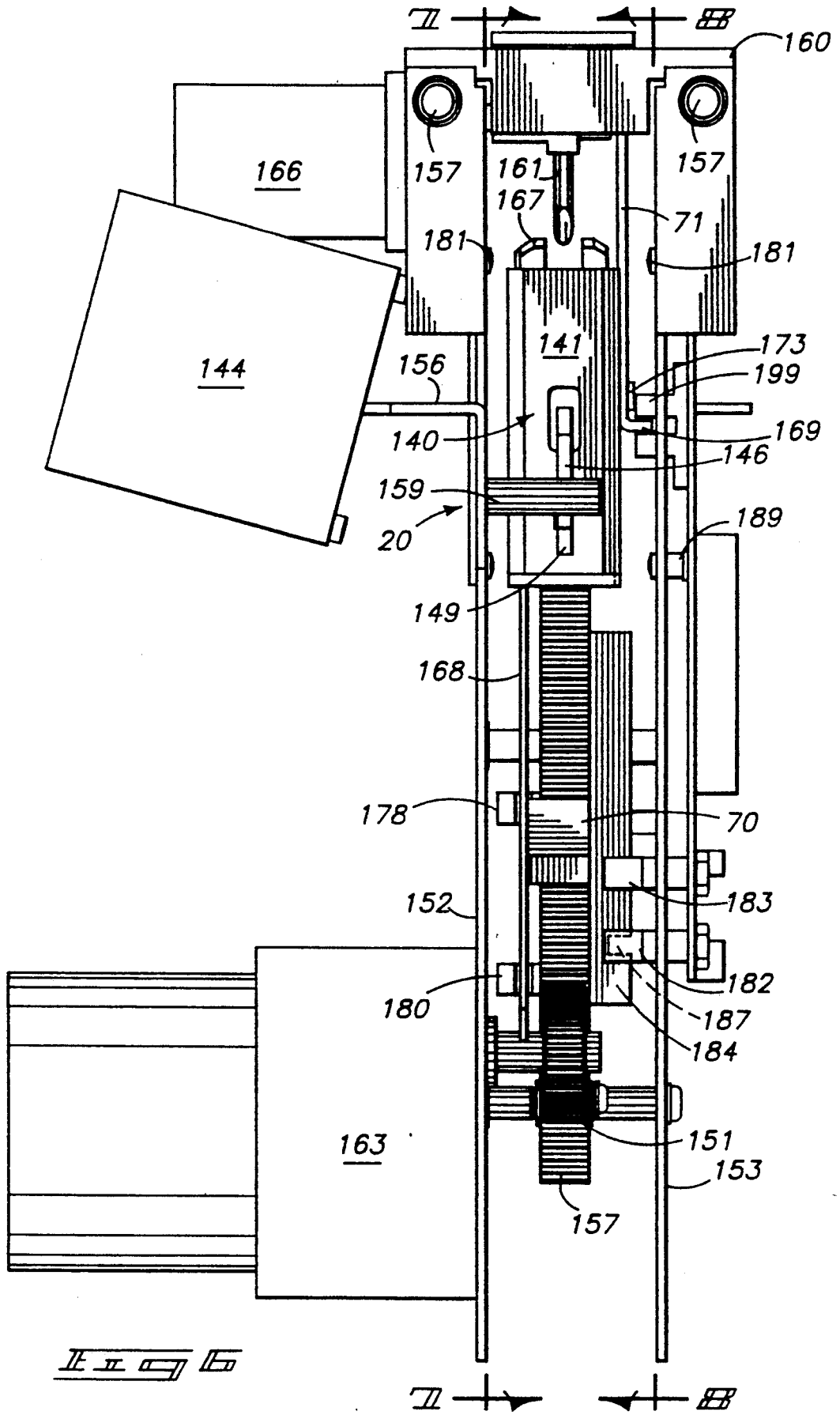
FIG. 6 is a front view of the sample tube entry port module, its front wall being removed.
Figure 7:
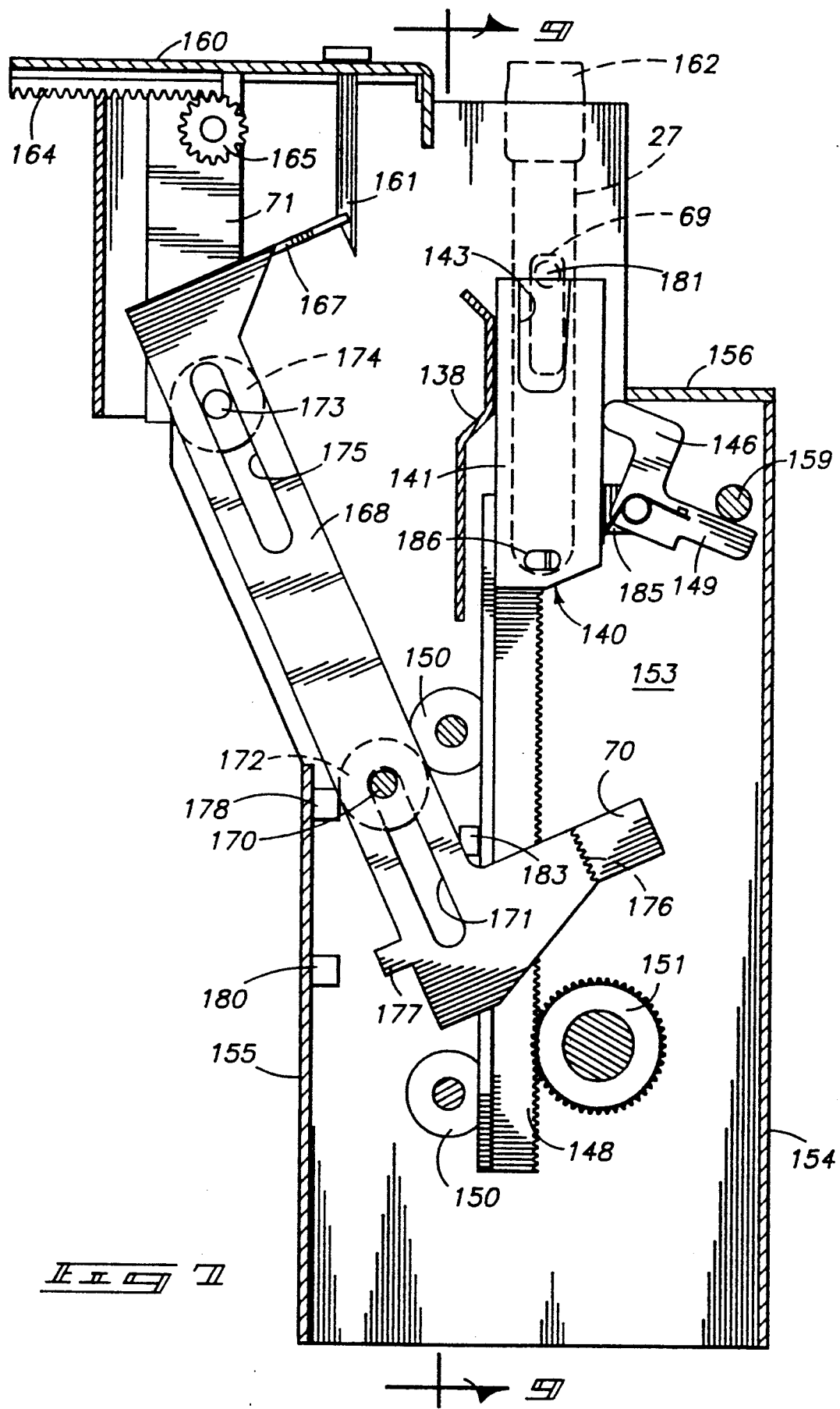
FIG. 7 is a sectional view taken along line 7—7 in FIG. 6.
Figure 8:
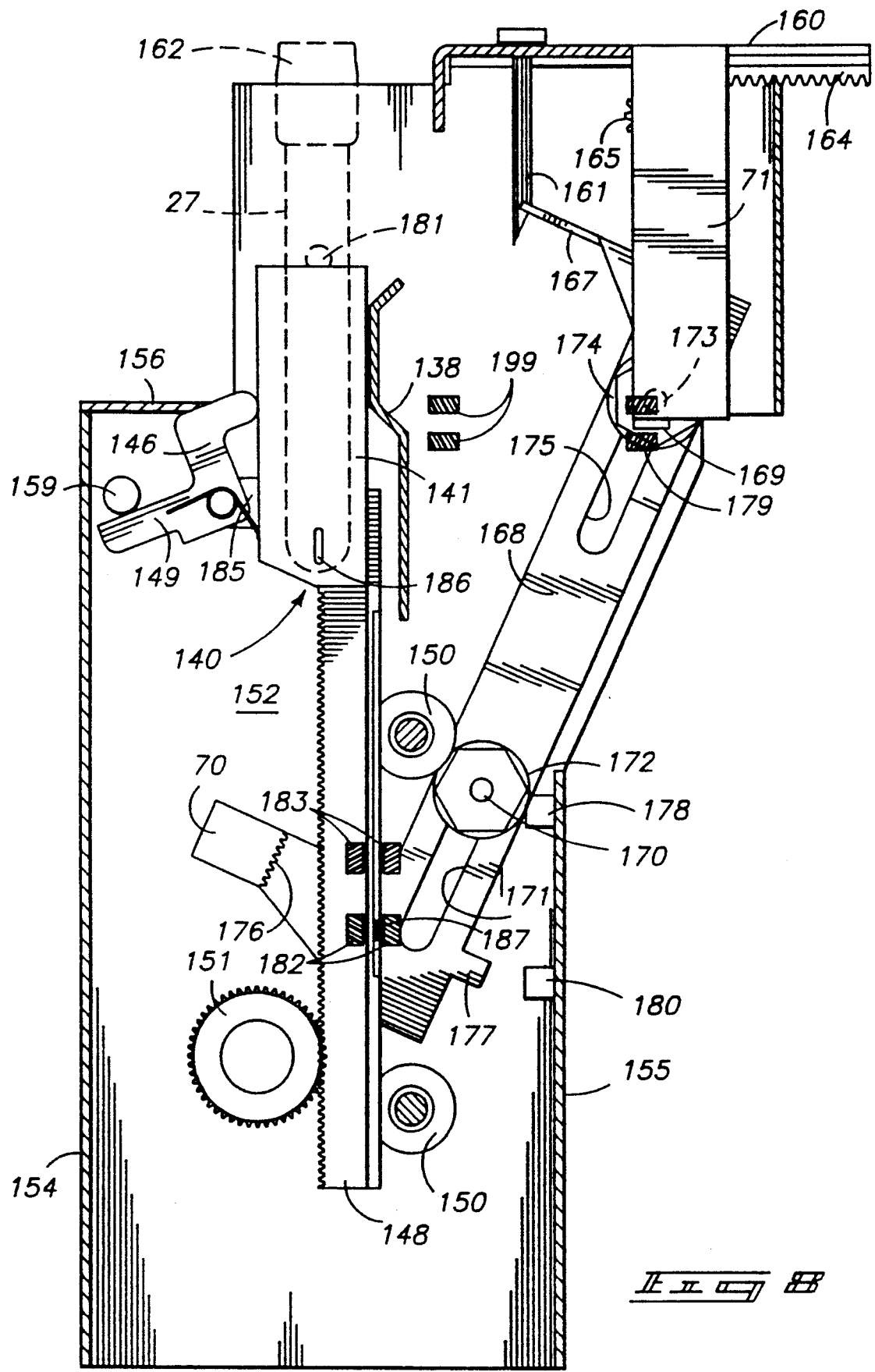
FIG. 8 is a sectional view taken along line 8—8 in FIG. 6.
Figure 9:
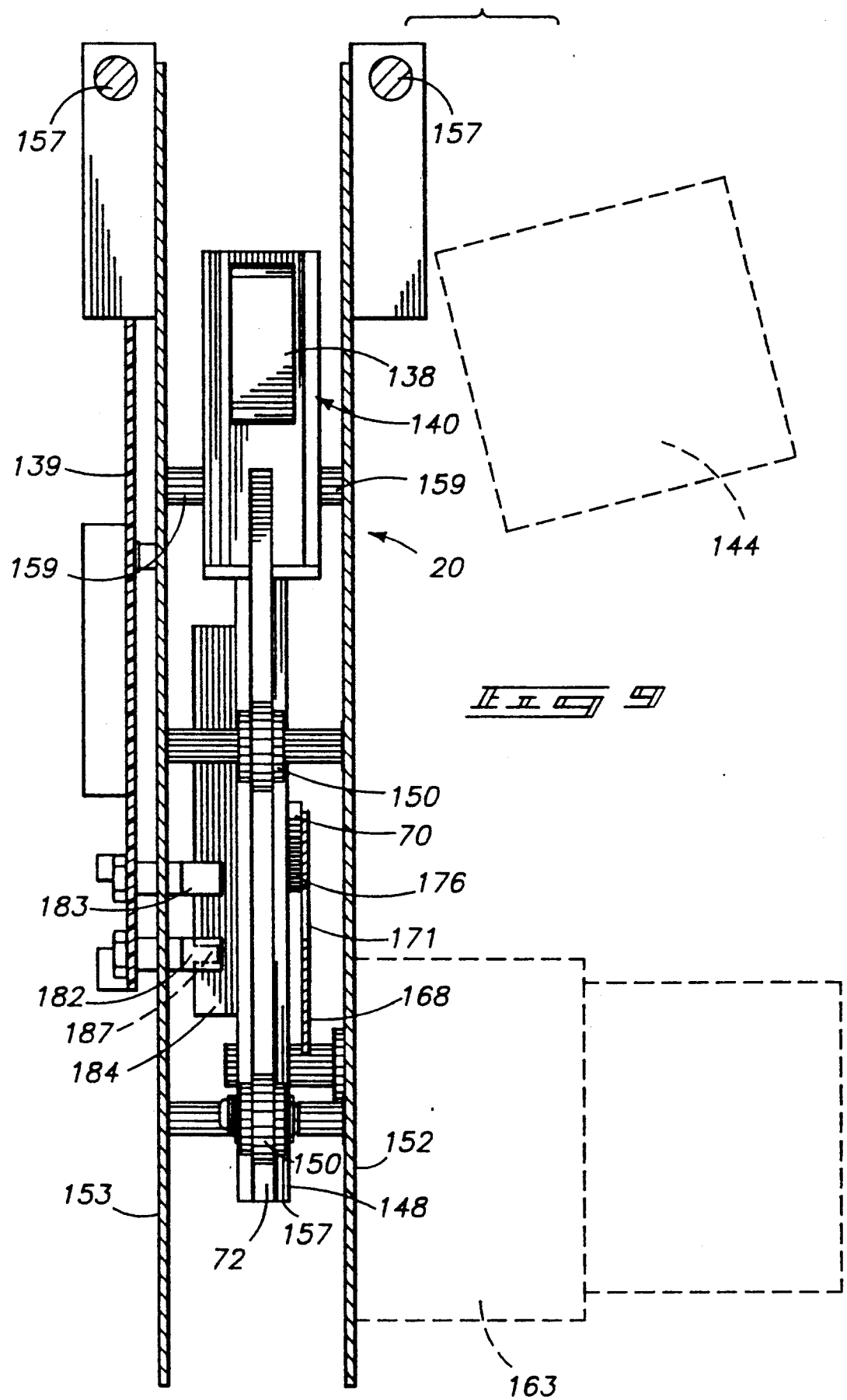
FIG. 9 is a sectional view taken along line 9—9 in FIG. 7.
Figure 10:
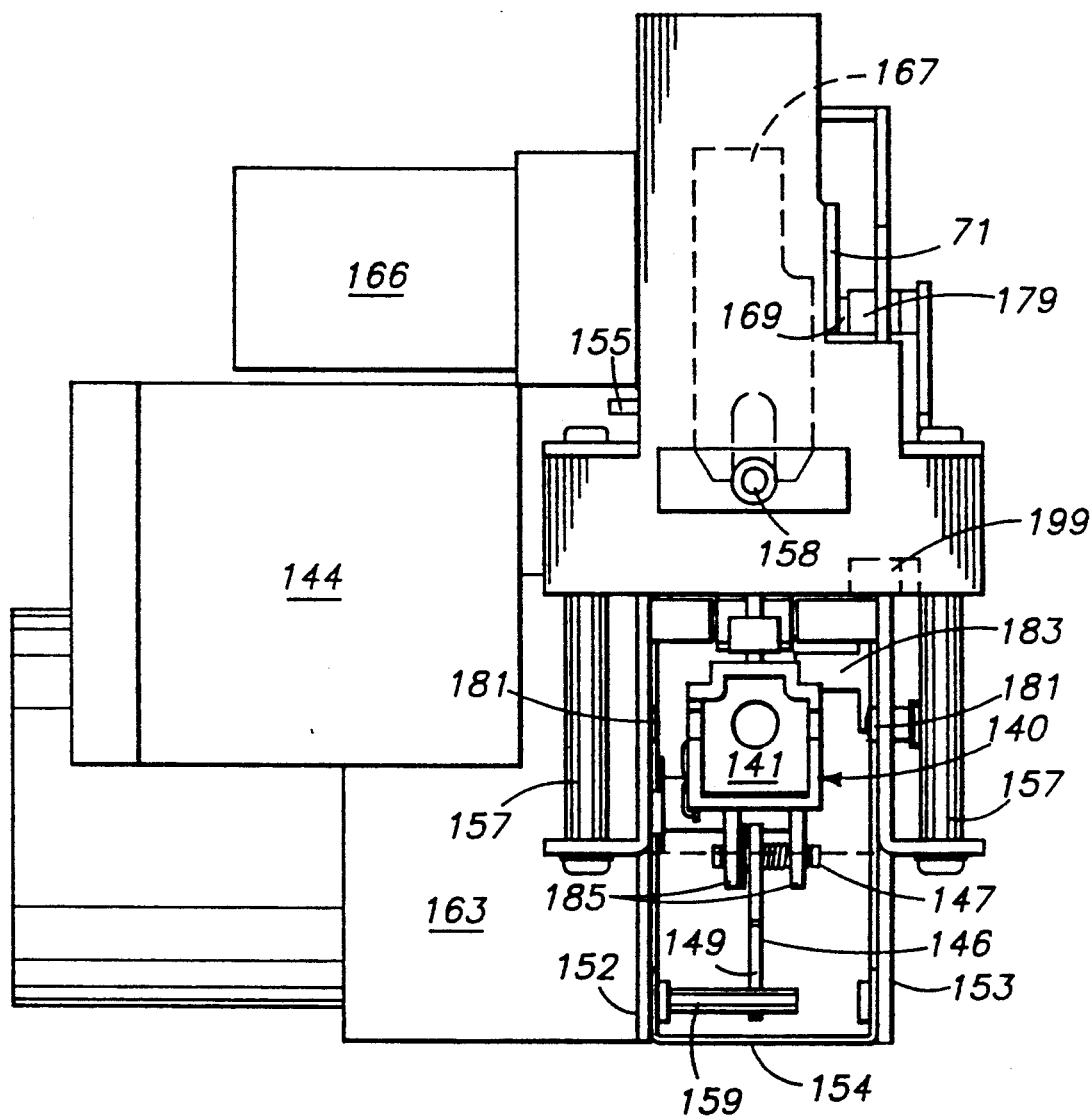
FIG. 10 is a top view of the module shown in FIG. 6.
Figure 11:
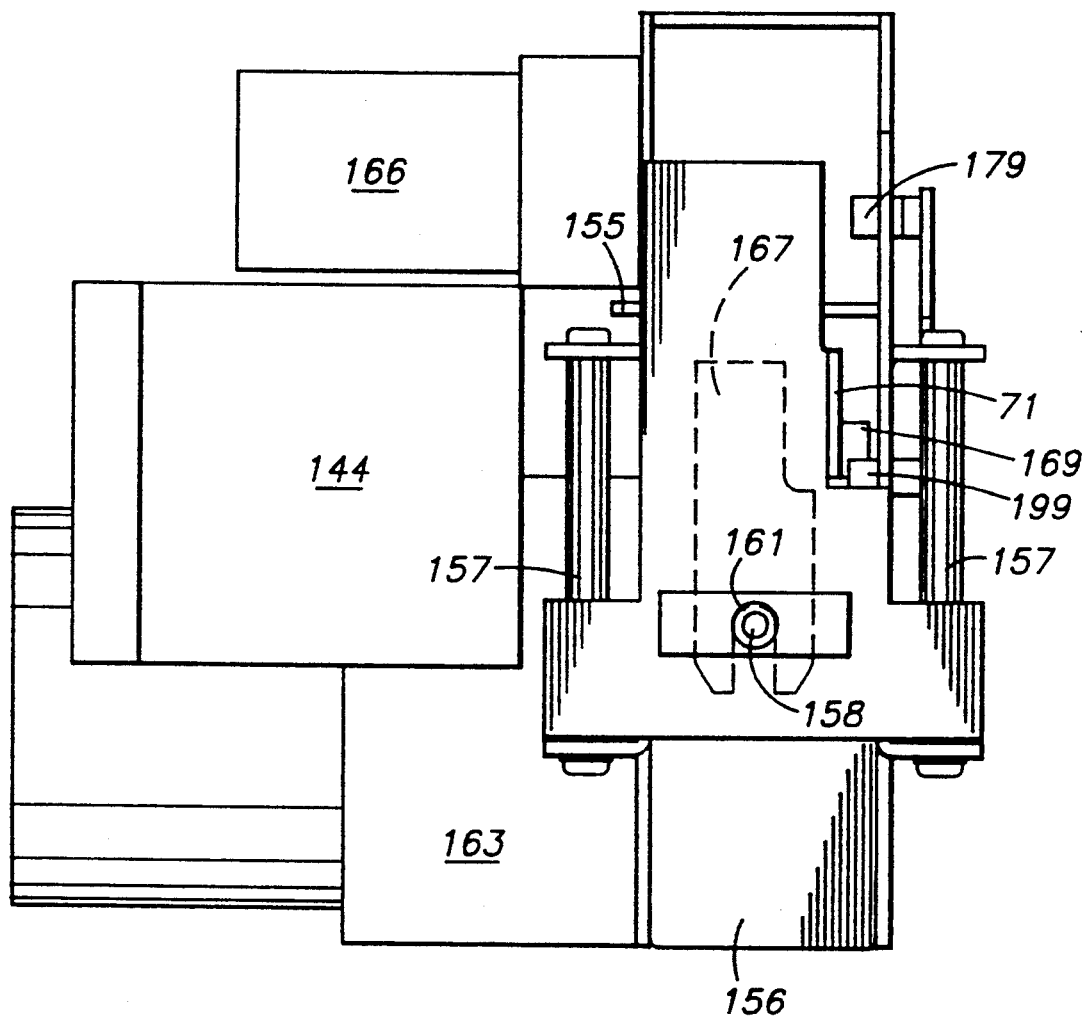
FIG. 11 is a top view with the cover in a closed position.

A longitudinal flag 184 protrudes to one side of rack 148 (see FIGS. 9 and 13). The upper end of flag 184 and an open notch 187 near its lower end are used to define predetermined limits of travel of ram 140 during its operation. They respectively act in conjunction with overlapping optical sensors 182 and 183 on the side wall 153 of the enclosure to detect maximum limits of vertical motion of ram 140 relative to the module framework. Line of sight sensors 181 are also arranged across side walls 152, 153, as shown in FIG. 6. The sensors 181 detect an intermediate position of each draw tube 27 as it is being raised vertically with the ram 140.

Cover 160 is reciprocated across the top of the enclosure by a rack 164 along its inside surface and a meshing drive gear 165. Gear 165 is powered by a DC motor 166.

The limits of movement of cover 160 are controlled by back and front sensors 179 and 199 mounted to a circuit board 159 located outwardly adjacent to side wall 153 of the module enclosure. A projecting horizontal flag 169 directed toward the adjacent side of cover 160 on a depending plate 71 is detected by the respective sensors 179 and 199 to terminate operation of motor 166 at the limits of cover movement. Detection of the positions of flag 169 assures that the cover 160 is either fully opened or fully closed for proper and safe operation of the chemical instrument 24.

Cover 160 mounts an open-ended puncture tube 161 designed to resealably puncture a conventional closure 162 on a draw tube 27. The inside diameter of puncture tube 161 is larger than the outside diameter of pipette 18. It presents an open aperture 158 for reception of the pipette 18 when the cover 160 is in its forward, or closed, position.

A bifurcated stripper 167 selectively overlies and engages the upper surface of a closure 162 on a draw tube 27 positioned within ram 140. Stripper 167 is centrally slotted at its front end to straddle the axial location of puncture tube 161 (see FIGS. 10 and 11). Its purpose is to prevent upward movement of closure 162 and draw tube 27 relative to ram 140 during removal of the puncture tube 161 and pipette 18 from a draw tube 27.

The stripper 167 is movably supported alongside the ram 140 by an integral extension 168. The lower end of extension 168 is pivotally guided on the supporting enclosure by a stationary shaft 170 received within a longitudinal slot 171. Shaft 17 is mounted to side wall 152 and mounts washers 172 that overlap the slot 171.

The upper end of extension 168 is similarly supported by a shaft 173 and overlapping washers 174. Shaft 173 is freely received within a second longitudinal slot 175 formed through extension 168. It is fixed to the plate 71 that extends downwardly from cover 160 next to side wall 153. Slot 175 within extension 168 is longer than slot 171. The extended length of slot 175 accommodates both the arcuate movement of extension 168 about the transverse axis of the stationary stub shaft 170 and the conjoint straight line movement of cover 160.

The lower end of extension 168 includes a straight section of gear teeth 176 formed across a transverse block 70 that faces toward rack 148. Gear teeth 176 are complementary to the teeth along rack 148. They are adapted to interfit with them to selectively lock extension 168 to rack 148 during operation of the sample tube entry port 20.

The lower end of extension 168 also includes a projecting flag 177. The position of flag 177 is detectable by upper and lower light sensors 178 and 180 on the rear wall 155 of the enclosure.

A stationary conductive metal plate 138 is spaced just slightly behind ram 140. It is supported on side wall 152. The elevation of plate 138 overlaps each draw tube 27 positioned within ram 140 at its uppermost position where the pipette 18 is inserted into it for sample access purposes.

The combination of the conductive plate 138 and conductive pipette 18 is used to capacitively sense the level of sample material within draw tube 27. By assuming that a draw tube 27 has the minimum diameter accommodated within the design limits of receptacle 141, measurement of the sample level can be converted by workstation 30 into usable sample volume information for inventory purposes. The calculation of remaining sample volume within a draw tube 27 also enables workstation 30 to guide the descending pipette 18 to a level adequate to remove the volume of sample needed for requisitioned tests.

Overview of Operation

The method for operating the chemistry analyzer 24 basically entails several randomly selectable steps. Its operation is timed about a repetitious sequence of cyclically transferring liquid from any selected container on the sample/reagent tray 15 to any selected cuvette 10 on the turntable 11, mixing liquids within the cuvettes on the turntable by turning it about the first axis, and rotating the turntable about the first axis. The timing of these steps is graphically depicted in FIG. 30.

The operational cycles of all components are timed to the repetitious cycle of operation of turntable 11. The turntable 11 is held stationary by motor 12 for a period during which a disposable cuvettes 10 can be delivered to the turntable 11 by operation of the cuvette delivery module. This in turn displaces a spent cuvette into a disposal container in the instrument. The turntable 11 is sequentially indexed to a stationary angular position about the first axis shown at X—X with a selected cuvette 10 positioned at a cuvette access station A. It is then turned about the axis while mixing or centrifuging the contents of cuvettes 10 mounted to it.

As the contents of cuvettes 10 are being centrifuged within turntable 11, the step of analyzing their contents at a location next to the turntable takes place within the optical system.

Liquid samples and reagents are supplied to turntable 11 by indexing the sample/reagent tray 15 about a second axis parallel to and spaced from the first axis to a stationary angular position with a selected container positioned at a container access station C. By moving probe arm 17 and pipette 18 along an arcuate path centered about a third axis that is parallel to the first axis and intersecting both the cuvette access station A and the container access station C, the chemistry instrument 24 can selectively transfer liquids from containers positioned on the tray 15 at the container access station C to cuvettes 10 positioned on the turntable 11 at the cuvette access station A. The workstation 30 is programmed so the step of moving the pipette 18 provides randomly accessible transfer of liquid from any container on the tray to any cuvette on the turntable in the time in which the turntable 11 is stationary during each cycle of operation.

Operation of the sample tube entry port to deliver samples from a draw tube occurs, on a demand basis, during the spin cycle of turntable 11 shown in FIG. 30.

The method of sample delivery to chemistry instrument 24 involves the steps of receiving a manually placed draw tube 27 beneath the puncture tube 161, moving the draw tube between a lowered position wherein the draw tube is clear of the puncture tube and a raised position wherein the puncture tube forms a temporary opening through a closure on the draw tube, and subsequently inserting the pipette 18 coaxially through the opening in the closure to access the interior of the draw tube. It further comprises the step of detecting the level of liquid in the draw tube 27 as it is approached by the pipette 18, using the capacitive sensing system.

The sequence of operations for the sample tube entry port can best be understood by reference to the simplified illustrations of FIGS. 16-28.

Figure 16:
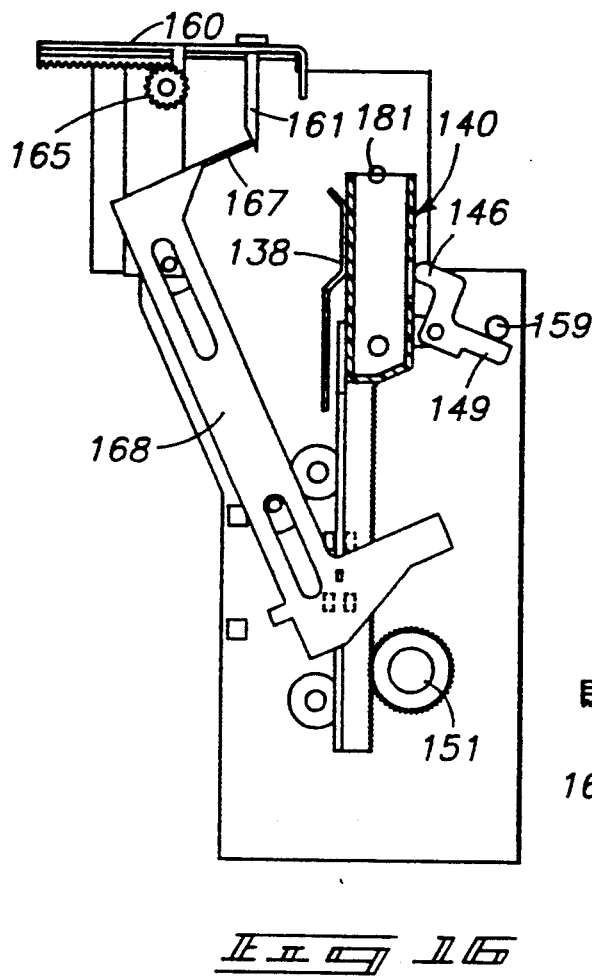

FIG. 16 shows ram 140 in its "home" position, where it receives and discharges successive draw tubes 27. This position of ram 140 is defined by the notch 187 within flag 184, which is detected by optical sensor 183.

Cover 160 is in its retracted or open position when ram 140 is "home". The tube clamp 146 is retracted from within the receptacle 141 at the "home" position, since the tab 149 is held downwardly by its engagement against rod 159. Stripper 167 is pivoted rearwardly and displaced from the top of ram 140, leaving the receptacle 141 open to receive an incoming draw tube 27. A draw tube 27 can then be loosely placed within ram 140 by an operator to initiate taking of a liquid sample from within it.

Figure 17:
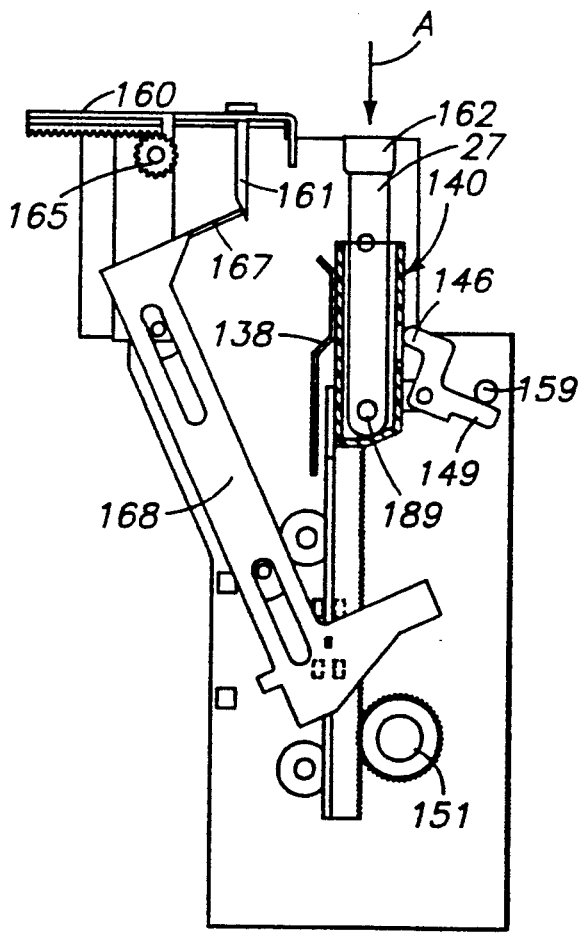

Reception of a draw tube 27, when inserted manually in the direction shown by arrow A in FIG. 17, is sensed by line of sight sensors 189 on the opposed side walls 152, 153. Sensors 189 will be trained through the transversely aligned apertures 186 in ram 140 while the ram 140 is stationary at its "home" position.

Figure 18:
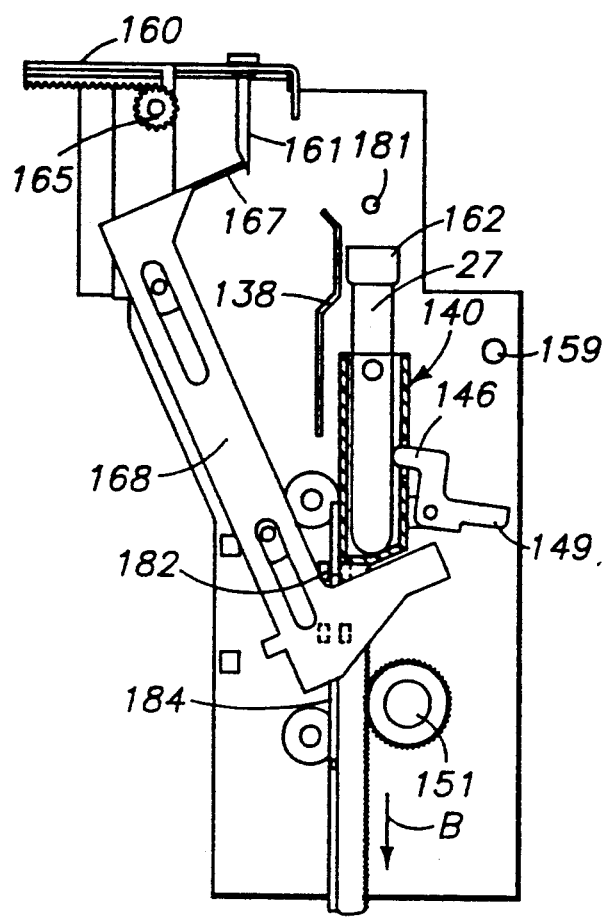

Detection of a draw tube 27 located within receptacle 141 by action of the sensors 189 initiates operation of motor 163 to move ram 140 downwardly within its surrounding enclosure in the direction shown by arrow B in FIG. 18. As ram 140 moves downwardly, the finger 149 on tube clamp 146 will separate from stationary rod 159. This allows tube clamp 146 to pivot inwardly by spring pressure to engage against the draw tube 27 through the aperture 145 formed in ram 140. The pressure of tube clamp 146 moves the draw tube 27 back between the vertical ribs 142 within the receptacle 141 to center and hold it securely within ram 140 regardless of its diameter or length.

Downward movement of ram 140 then continues in the direction of arrow B to its bottom limit of movement (FIG. 18). This extreme lower position is defined by detection of the upper end of flag 184 by sensor 182.

Figure 19:
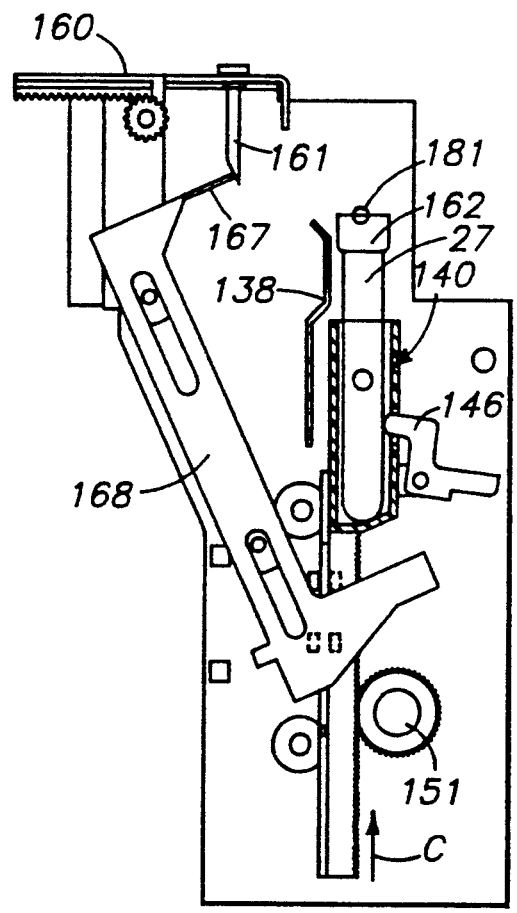

When the bottom limit of movement of ram 140 is reached, the controls for motor 163 will be reversed to impart upward movement to it in the direction shown by arrow C in FIG. 19. This upward movement will continue until the top surface of the closure 162 on the draw tube 27 is sensed by line of sight sensors 181 trained between the side walls 152, 153 of the enclosure.

The intermediate limit of upward motion for a specific draw tube 27 is illustrated in FIG. 19. It is to be noted that this limit of movement is defined by the top surface of the closure 162 and is independent of the axial length of draw tube 27.

After the draw tube 27 has been raised to its intermediate elevated position, as shown in FIG. 19, a bar coded label or other readable indicia along the side of the draw tube 27 is scanned by digital scanner 144. The scanned identification data can then be transmitted to the programmed workstation 30 to access requisition information supplied with respect to the sample. The scanned data also permits the identification of the sample to be verified. By matching the identification data and requisition data for a specific sample, the analyzer can then program the tests to be conducted upon it and compute the amount of sample that must be removed from the draw tube 27 for such tests.

if the sample identification and requisition information is not matched in workstation 30, control signals supplied from it to motor 163 will override photocell detector 181 and cause the ram 140 to return to its "home" position, as shown in FIG. 17, where the draw tube 27 can be manually removed from the sample tube entry port. At this point the operator can remove and rotate the reinserted draw tube 27 to align encoded indicia along its side with the slot 143 for access by scanner 144 or can manually input identifying data through keyboard 32. Replacement of draw tube 27 within receptacle 141 will cause the steps described with respect to FIGS. 17-19 to be repeated until the sample identification sequence is successfully completed.

Assuming that a draw tube 27 and inputted requisition data have been properly identified, either through scanner 144 or keyboard 32, the removal of sample liquid from within the draw tube 27 is then carried out automatically with no further manual intervention.

Figure 20:
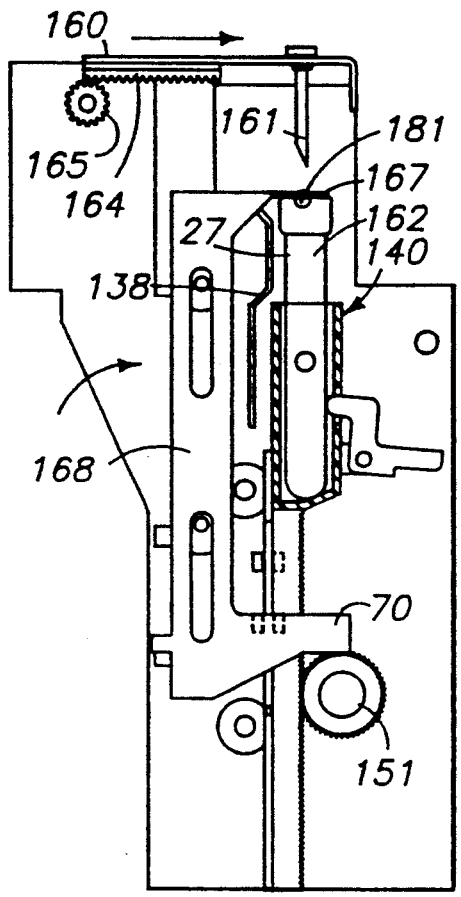

The next step in the procedure involves forward movement of cover 160 in the direction shown by arrow D in FIG. 20. This cover motion, which is initiated under control of workstation 30, prevents further manual access to the draw tube 27. Closing of cover 160 also axially aligns puncture tube 161 above closure 162.

As closing movement of cover 160 occurs, the stripper 167 and extension 168 will be pivoted about stub shaft 170 by the connection between shaft 173 and extension 168 to bring extension 168 into a vertical position parallel with rack 148. This causes gear teeth 176 to engage and be interfitted with the teeth along the front of rack 148. Because extension 168 will then be resting at the upper end of slot 171, extension 168 will be clamped to rack 148 in a predetermined elevational relationship position with stripper 167 immediately adjacent to the previously-referenced elevation of the upper surface of stopper 162. In this position, both the upper surface of the closure 162 on draw tube 27 and the stripper 167 are elevationally referenced with respect to the enclosure—closure 162 by operation of sensors 181, and stripper 167 by the engagement between slot 171 and stub shaft 170. They can thus be accurately positioned relative to one another regardless of draw tube height.

Figure 21:
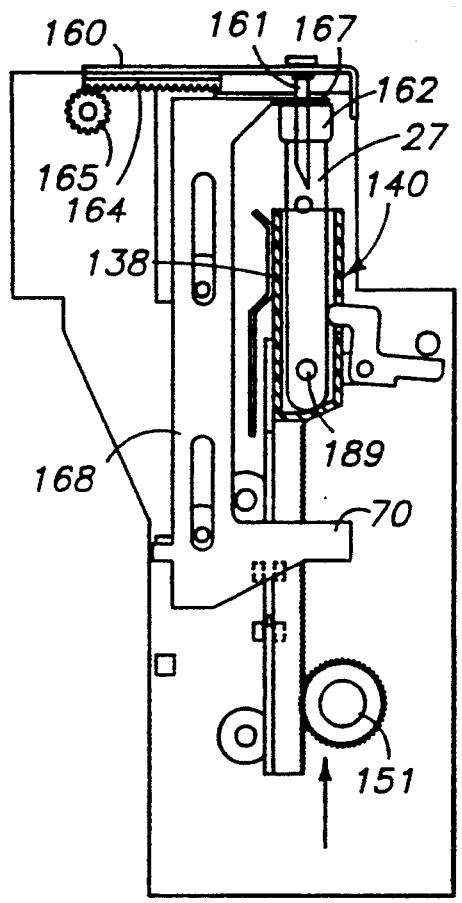

Puncturing of closure 162 is accomplished by raising the engaged ram 140 and extension 168 in unison through operation of motor 163. This elevational motion, in the direction shown by arrow E in FIG. 21, is limited by sensor 178. Sensor 178 detects the upper limit of movement of extension 168 when it is blocked by flag 177, as shown in FIG. 21.

After closure 162 has been punctured, the probe arm 17 is pivoted about its axis on the chemistry instrument 24 in the manner illustrated by arrow F in FIG. 22. The movements of probe arm 17 occur under control of the programmed workstation 30 to align pipette 18 above aperture 158 (FIG. 22). Probe arm 17 can then be lowered in the direction shown by arrow G in FIG. 23 to insert pipette 18 downwardly into draw tube 27. The amount of liquid to be drawn from the draw tube 27 is governed by microprocessor control and instructions programmed into the workstation 30 for a specific test requisition.

Following receipt of the liquid sample, ram 140 is initially moved downwardly in the direction shown by arrow H in FIG. 24 until flag 177 is detected by sensor 180. The straddling nature of the bifurcated stripper 167 resting against the upper surface of closure 162 assures against displacement of the closure 162 with respect to draw tube 27 as they are lowered relative to the stationary puncture tube 161. It is to be noted that pipette 18 is stationary and partially remains within the draw tube 27 during withdrawal of puncture tube 161.

After closure 162 has been lowered to the position shown in FIG. 24, where it is clear of puncture tube 161, probe arm 17 can be raised in the direction shown by arrow I in FIG. 25 to retract pipette 18 upwardly through aperture 158 in cover 160. The resealing closure 162 will then wipe the outer surfaces of pipette 18 to prevent liquid from dripping from the exterior of the pipette as it is lifted upwardly. Pipette 18 is then freed for later movement about the chemistry instrument 24.

Figure 26:
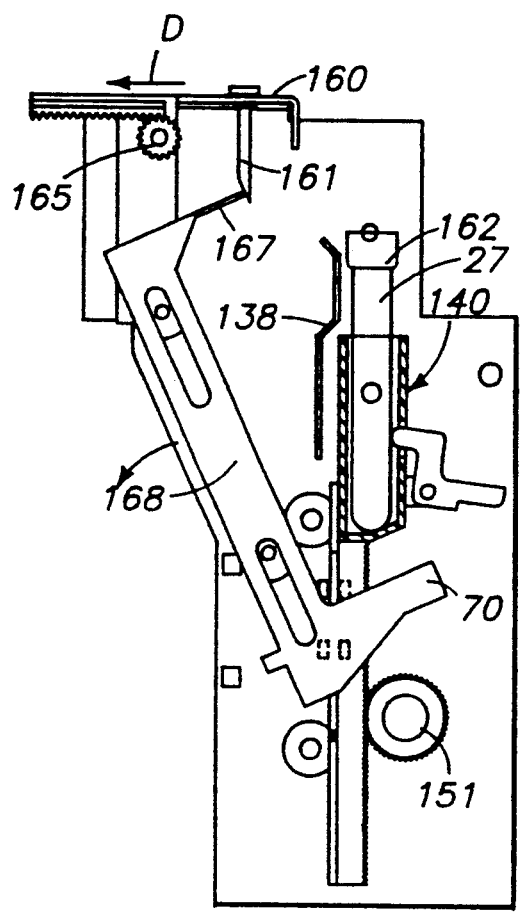

Following lifting of pipette 18, the workstation 30 operates motor 166 to move cover 160 rearwardly in the direction shown by arrow J in FIG. 26. Retraction of cover 160 also separates gear teeth 176 from rack 148, returning the stripper to its original position.

Figure 27:
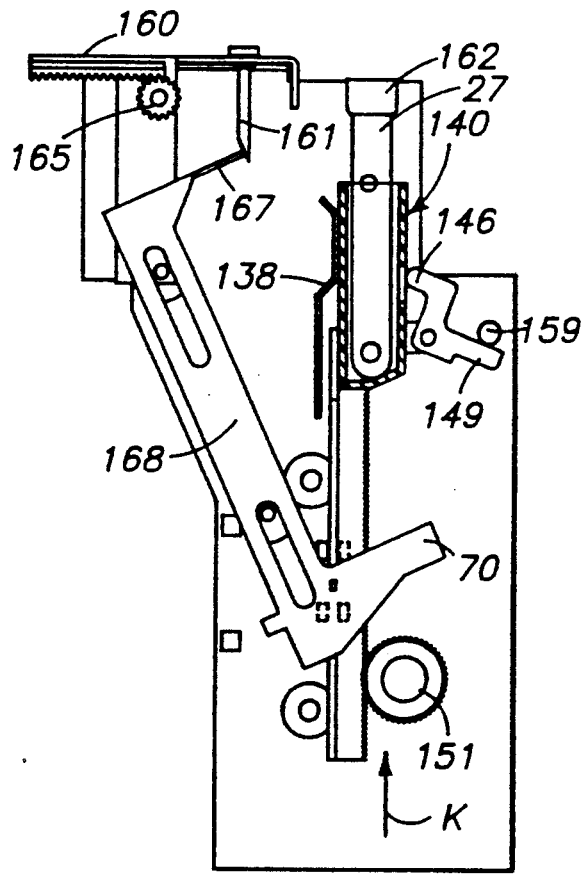
Figure 28:
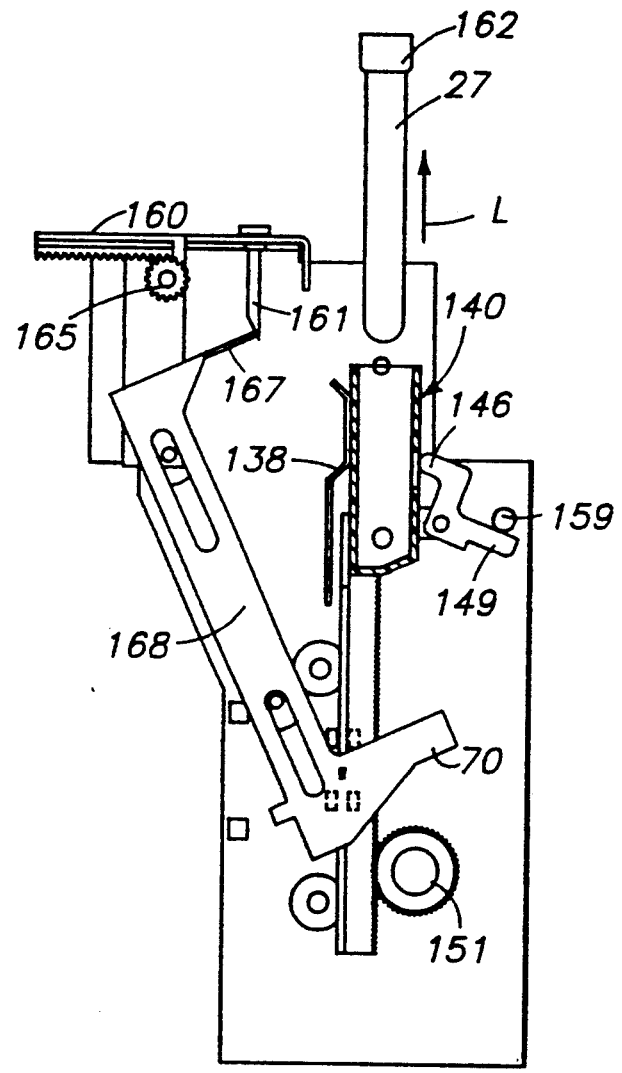

After retraction of cover 160 has been completed, motor 163 is again activated to raise ram 140 in the direction shown by arrow K in FIG. 27 to its "home" position, where tube clamp 146 is released. The resealed draw tube 27 can then be manually lifted from ram 140 in the direction shown by arrow L in FIG. 28, leaving ram 140 again in its "home" position, where it is ready for reception of a subsequent draw tube. Successive draw tubes can be manually supplied to the chemistry instrument 24 at any time during its operation.

Controller System

Figure 29:
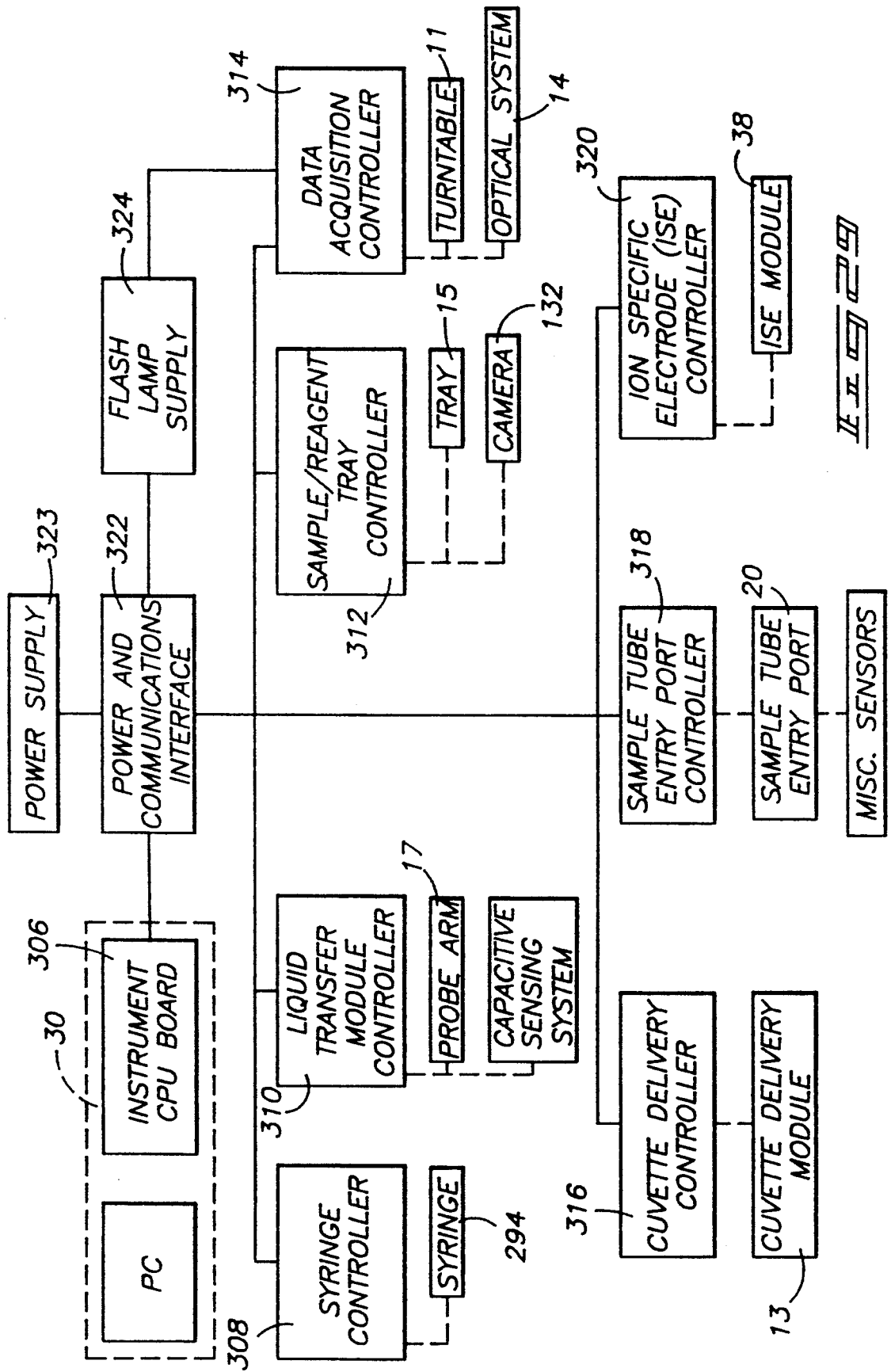
FIG. 29 is a block diagram of the instrument controllers.

The computerized controller system for the various modules includes within the chemistry instrument 24 is diagrammatically illustrated in FIG. 29. The control circuitry shown in FIG. 29 is that associated with a single chemistry instrument 24. Where two chemistry instruments 24 are used in a single installation, the illustrated components (other than workstation 30) will be duplicated for each instrument.

Scheduling of physical operations to be carried out in the chemistry instrument 24 is controlled by an instrument central processing unit (CPU) circuitboard 306. The instrument CPU board 306, located physically within workstation 30, is programmed to schedule the randomly available operations of the chemistry instrument modules as permitted by the status of its affected modular components and as required by a requisitioned assay. Board 306 includes a suitable microprocessor and memory devices for storing logic and scheduling programs required to operate the chemistry instrument.

The control system for each chemistry instrument 24 includes a distributed family of controller microprocessors located within its various modules. In the preferred embodiment shown in FIG. 29, there are seven microprocessor controllers associated with operation of the instrument components. Their respective operational functions and associated modular components are as follows:

Syringe Controller 308—directly controls operation of syringe 294. Controller 308 monitors the linear position of the syringe piston by means of signals supplied by an optical sensor (not shown). It also operates control valves associated with syringe 294.

Liquid Transfer Module Controller 310—moves probe arm 17 both vertically and angularly through use of operator 19. Photocell sensors associated with probe arm 17 and operator 19 provide signals indicative of the preset vertical and angular positions of probe arm 17. Controller 310 also maintains desired liquid temperatures for liquids in the tubing arranged along the probe arm 17 that leads to pipette 18 through monitored operation of a heating element. It additionally controls operation of the capacitive sensing system.

Sample/Reagent Tray Controller 312—operates motor 16 to position sample/reagent tray 15 about its axis. It monitors sensors to index tray 15 at a selected angular position for pipette access to a selected container. It also controls operation of reagent bottle label readers located under the sample/reagent tray 15. The sample/reagent tray controller 312 is further responsible for maintaining suitable reagent temperatures through selective operation of cooling elements (not shown) associated with tray 15 and is connected to a sensor which selectively detects the presence of cups 35 within a ring segment 26.

Data Acquisition Controller 314—Controls rotation and indexing of turntable 11 through operation of motor 12. Indexing information is supplied to it from sensors next to the turntable 11. Controller 314 also operates the elements included within optical system 14 and relays resulting absorbance and fluorescence data for tested samples.

Cuvette Delivery Controller 316—Operates the components of cuvette delivery module 13. It further provides temperature controls for heating and cooling devices (not shown) associated with turntable 11 for maintaining desired reaction temperatures during its operation.

Sample Tube Entry Port Controller 318—Governs operation of sample tube entry port 20. It receives signals from line of sight sensors 189 directed through apertures 186 within ram 140 to detect the presence of each draw tube as it is manually inserted into the chemistry instrument 124. Controller 318 also monitors all of the various sensors that limit and control movement of ram 140 and cover 160, and coordinates movement of the components within sample tube entry port 20 with movement of probe arm 17. In addition, it controls operation of scanner 144 that reads information from bar coded labels or other optical data on each incoming draw tube. Controller 318 further monitors miscellaneous activities required for effective use of the chemistry instrument 24, including conditions of the diluent supply within container rack 28 and the status of the waste liquid container, segment access port 7, tray access cover 8, cover 160, various access doors, and the cuvette disposal container.

Ion Specific Electrode (ISE) Controller 320—Controls operation of the ISE module 38 to test samples for the presence of electrolytes such as sodium, potassium, chloride, lithium and calcium. The operational functions of this controller are dictated by conventional operation of the ISE module 38 and are well known to those skilled in such technology.

In addition to the listed controllers, the chemistry instrument 24 has a power and communications interface 322 for all the modules included within it and with a flash lamp supply 324 that powers and operates a light source within optical system 14. The power and communications interface 322 is operatively connected to the instrument CPU board 306 and to a suitable power supply 323 capable of providing the electrical power needed by the various motors and electronic components of the chemistry instrument 24.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method for accessing the contents of a draw tube after it has been manually delivered to a sample access station of a chemistry instrument including a probe arm supporting a downwardly-extending open pipette, comprising the following steps:
   receiving a manually placed draw tube within an elevationally movable receptacle;
   selectively lowering the receptacle and draw tube to a first predetermined elevation;
   subsequently raising the receptacle and draw tube to an intermediate elevated position at which an upper surface of a closure in the draw tube is positioned at an second predetermined elevation;
   positioning a hollow puncture tube above the closure;
   locking a bifurcated stripper relative to the receptacle with the stripper immediately adjacent to the elevation of the upper surface of the closure to match the elevational position of the stripper to the overall height of the draw tube and closure;
   raising the receptacle and draw tube to a third predetermined elevation at which the closure is punctured by the puncture tube; and
   inserting a pipette through the puncture tube and into the interior of the draw tube to access its contents.

2. The method for accessing the contents of a draw tube as set forth in claim 1, comprising the following additional step prior to the step of selectively lowering the receptacle and draw tube:
   selectively urging the draw tube into engagement against upright surfaces at the inside of the receptacle to thereby accommodate draw tubes of differing diameters.

3. The method for accessing the contents of a draw tube as set forth in claim 1, comprising the following additional sequential steps:
   first moving the receptacle and locked stripper downwardly until the closure is elevationally clear of the puncture tube; and
   then raising the pipette upwardly to elevationally retract it from the closure and puncture tube and free it for subsequent movement.

4. The method for accessing the contents of a draw tube as set forth in claim 1, comprising the following additional sequential steps:
   first moving the receptacle and locked stripper downwardly until the closure is elevationally clear of the puncture tube;
   then raising the pipette upwardly to elevationally retract it from the closure and puncture tube and free it for subsequent movement;
   releasing the bifurcated stripper from the receptacle and moving it to a location clear of the receptacle; and
   raising the receptacle and draw tube to an elevation at which the draw tube can be manually removed from within the receptacle.

5. A sample tube entry port for accessing the contents of a draw tube after it has been manually delivered to a sample access station of a chemistry instrument including a probe arm supporting a downwardly-extending open pipette movable about an arcuate path centered about a fixed reference axis, comprising:
   tubular puncturing means for temporarily forming an opening through a closure on a manually-delivered draw tube placed in the sample tube entry port means to make the interior of the draw tube accessible by subsequently inserting the pipette of the probe arm means coaxially through the puncturing means;
   ram means including an upwardly open receptacle positioned on the chemistry instrument at an elevation below that of the puncturing means for receiving and transversely centering a manually placed draw tube relative to the puncturing means and for elevationally moving the draw tube in directions parallel to the reference axis between a lowered position wherein the draw tube and receptacle are clear of the puncturing means and a raised position wherein the puncturing means forms a temporary opening through a closure at the top of a draw tube within the receptacle in preparation for subsequent coaxial insertion of the pipette; and a bifurcated stripper including an extension that can be releasably engaged with the ram means to selectively lock the extension to the ram means when the stripper is in its extended position, the extension being pivotally mounted on the chemistry instrument for movement of the stripper between a retracted position clear of the ram means and an extended position overlying the ram means and straddling the axial location of the puncturing means.

6. The sample tube entry port of claim 5, wherein the ram means includes a vertical rack having transverse teeth in meshing engagement with a powered gear;

the extension having a section of gear teeth complementary to the teeth along the rack and adapted to interfit with the teeth so as to selectively lock the extension to the rack means during operation of the sample tube entry port.

7. The sample tube entry port of claim 5, wherein the extension is pivotally mounted by a stationary shaft received within a longitudinal slot formed through the extension, the slot accommodating upward motion of the ram means and stripper when the extension is locked to the ram means.

8. The sample tube entry port of claim 5, further comprising:

control means for selectively lowering the ram means relative to the puncturing means to a first predetermined elevation and subsequently raising the ram means to an elevated position with the upper surface of a closure in a draw tube in the receptacle being at an elevation immediately below that of the bifurcated stripper when in its extended position.

9. The sample tube entry port of claim 5, wherein the upwardly-open receptacle includes upright surfaces adapted to engage draw tubes of differing diameters located within the receptacle; and tube clamp means mounted on the receptacle for selectively moves a draw tube into engagement with the upright surfaces.

10. The sample tube entry port of claim 5, wherein the upwardly-open receptacle includes a transverse aperture and upright interior ribs facing the aperture and adapted to engage one side of draw tubes of differing diameters located within the receptacle; and a tube clamp mounted on the receptacle selectively projecting through the aperture; and biasing means operably connected between the receptacle and the tube clamp for moving the tube clamp through the aperture and urging a draw tube into engagement with the upright ribs.

11. The sample tube entry port of claim 5, further comprising:

a cover movably mounted on the chemistry instrument at the sample access station, the cover being movable between an open position clear of the ram means and a closed position overlying it;

the puncturing means being fixed to and extending downwardly from the underside of the cover.

12. The sample tube entry port of claim 5, further comprising:

a cover movably mounted on the chemistry instrument at the sample access station, the cover being movable between an open position clear of the ram means and a closed position overlying it;

the puncturing means being fixed to and extending downwardly from the underside of the cover; and pivot means interconnecting the cover and the bifurcated stripper for shifting the stripper between its retracted and extended positions in response to movement of the cover between its open and closed positions, respectively.

* * * * *